United States Patent
Peer

(10) Patent No.: US 10,179,113 B2
(45) Date of Patent: *Jan. 15, 2019

(54) CELL-TARGETING NANOPARTICLES COMPRISING POLYNUCLEOTIDE AGENTS AND USES THEREOF

(71) Applicant: RAMOT AT TEL-AVIV UNIVERSITY LTD., Tel Aviv (IL)

(72) Inventor: Dan Peer, Kiryat Ono (IL)

(73) Assignee: RAMOT AT TEL-AVIV UNIVERSITY LTD., Tel Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/402,444

(22) Filed: Jan. 10, 2017

(65) Prior Publication Data

US 2017/0143641 A1    May 25, 2017

Related U.S. Application Data

(63) Continuation of application No. 13/388,161, filed as application No. PCT/IL2010/000614 on Jul. 29, 2010, now Pat. No. 9,574,210.

(30) Foreign Application Priority Data

Jul. 31, 2009 (GB) .................................... 0913442.0
Jul. 29, 2010 (WO) .................. PCT/IL2010/000614

(51) Int. Cl.
| | | |
|---|---|---|
| C12N 15/113 | (2010.01) | |
| A61K 9/50 | (2006.01) | |
| A61K 9/51 | (2006.01) | |
| C12N 15/87 | (2006.01) | |
| C12N 15/88 | (2006.01) | |
| A61K 9/127 | (2006.01) | |
| B82Y 5/00 | (2011.01) | |
| A61K 47/68 | (2017.01) | |
| A61K 47/69 | (2017.01) | |

(52) U.S. Cl.
CPC .......... *A61K 9/5161* (2013.01); *A61K 9/1272* (2013.01); *A61K 9/5123* (2013.01); *A61K 47/6849* (2017.08); *A61K 47/6935* (2017.08); *A61K 47/6939* (2017.08); *B82Y 5/00* (2013.01); *C12N 15/113* (2013.01); *C12N 15/87* (2013.01); *C12N 15/88* (2013.01); *C12N 2310/14* (2013.01); *C12N 2310/141* (2013.01); *Y10T 428/2982* (2015.01); *Y10T 428/2991* (2015.01)

(58) Field of Classification Search
None
See application file for complete search history.

(56) References Cited

U.S. PATENT DOCUMENTS

| | | |
|---|---|---|
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,235,871 A | 11/1980 | Papahadjopoulos et al. |
| 4,666,828 A | 5/1987 | Gusella |
| 4,683,202 A | 7/1987 | Mulls |
| 4,801,531 A | 1/1989 | Frossard |
| 4,879,219 A | 11/1989 | Wands et al. |
| 4,898,735 A | 2/1990 | Barenholz et al. |
| 4,902,512 A | 2/1990 | Ishigami et al. |
| 4,927,637 A | 5/1990 | Morano et al. |
| 5,011,771 A | 4/1991 | Bellet et al. |
| 5,143,713 A | 9/1992 | Phillips et al. |
| 5,192,659 A | 3/1993 | Simons |
| 5,272,057 A | 12/1993 | Smulson et al. |

(Continued)

FOREIGN PATENT DOCUMENTS

| | | |
|---|---|---|
| JP | H09-511252 A | 11/1997 |
| JP | 2002-537102 | 11/2002 |

(Continued)

OTHER PUBLICATIONS

European Application No. 13778205.8, Extended European Search Report, dated Jul. 29, 2015, 5 pages.
European Application No. 02761287.8, Supplementary European Search Report, dated Feb. 8, 2010, 3 pages.
International Search Report for International Application No. PCT/US2002/025178 dated Dec. 20, 2002, 1 page.
International Search Report and Written Opinion for International Application No. PCT/IL2010/000614 dated Jan. 21, 2011, 14 pages.
International Preliminary Report on Patentability for International Application No. PCT/IL2010/000614 dated Jan. 31, 2012, 9 pages.

(Continued)

*Primary Examiner* — Richard A Schnizer
(74) *Attorney, Agent, or Firm* — Browdy and Neimark, PLLC

(57) ABSTRACT

A method of generating a particle is disclosed, the particle being for delivery of a polynucleotide to a target cell. The method comprises (a) contacting the polynucleotide with a composition comprising cationic molecules, wherein the cationic molecules condense the polynucleotide by electrostatic interactions to generate a complex, wherein the cationic molecules are not comprised in a liposome; and (b) covalently binding the complex to a targeting moiety at a pH equal to or below about 4.5, thereby generating the particle for delivery of the polynucleotide agent to the target cell. Use of the particles and compositions comprising same are also disclosed.

14 Claims, 11 Drawing Sheets

Specification includes a Sequence Listing.

(56) References Cited

U.S. PATENT DOCUMENTS

| | | |
|---|---|---|
| 5,281,521 A | 1/1994 | Trojanowski et al. |
| 5,401,511 A | 3/1995 | Margalit |
| 5,614,506 A | 3/1997 | Falk et al. |
| 5,624,839 A | 4/1997 | Yada et al. |
| 5,637,483 A | 6/1997 | Dranoff et al. |
| 5,639,738 A | 6/1997 | Falk et al. |
| 5,674,857 A | 10/1997 | Falk et al. |
| 5,733,892 A | 3/1998 | Sakurai et al. |
| 5,783,566 A | 7/1998 | Mislick |
| 5,792,753 A | 8/1998 | Falk et al. |
| 5,811,410 A | 9/1998 | Falk et al. |
| 5,817,642 A | 10/1998 | Falk et al. |
| 5,824,658 A | 10/1998 | Falk et al. |
| 5,827,834 A | 10/1998 | Falk et al. |
| 5,830,882 A | 11/1998 | Falk et al. |
| 5,834,444 A | 11/1998 | Falk et al. |
| 5,847,002 A | 12/1998 | Willoughby et al. |
| 5,852,002 A | 12/1998 | Falk et al. |
| 5,910,489 A | 6/1999 | Falk et al. |
| 5,914,314 A | 6/1999 | Falk et al. |
| 5,914,322 A | 6/1999 | Falk et al. |
| 5,922,350 A | 7/1999 | Janoff et al. |
| 5,929,048 A | 7/1999 | Falk et al. |
| 5,932,560 A | 8/1999 | Falk et al. |
| 5,942,498 A | 8/1999 | Falk et al. |
| 5,962,433 A | 10/1999 | Falk et al. |
| 5,972,906 A | 10/1999 | Asculai et al. |
| 5,977,088 A | 11/1999 | Harper et al. |
| 5,985,850 A | 11/1999 | Falk et al. |
| 5,985,851 A | 11/1999 | Falk et al. |
| 5,990,095 A | 11/1999 | Falk et al. |
| 5,990,096 A | 11/1999 | Asculai et al. |
| 6,017,900 A | 1/2000 | Falk et al. |
| 6,022,866 A | 2/2000 | Falk et al. |
| 6,048,844 A | 4/2000 | Falk et al. |
| 6,069,135 A | 5/2000 | Falk et al. |
| 6,087,344 A | 7/2000 | Falk et al. |
| 6,103,704 A | 8/2000 | Falk et al. |
| 6,114,314 A | 9/2000 | Falk et al. |
| 6,136,793 A | 10/2000 | Falk et al. |
| 6,140,312 A | 10/2000 | Falk et al. |
| 6,147,059 A | 11/2000 | Falk et al. |
| 6,194,392 B1 | 2/2001 | Falk et al. |
| 6,197,332 B1 | 3/2001 | Zuckermann |
| 6,207,178 B1 | 3/2001 | Westesen et al. |
| 6,218,373 B1 | 4/2001 | Falk et al. |
| 6,348,185 B1 | 2/2002 | Piwnica-Worms |
| 6,593,308 B2 | 7/2003 | Szoka |
| 6,986,902 B1 | 1/2006 | Chen et al. |
| 7,544,374 B2 | 6/2009 | Margalit et al. |
| 8,277,847 B2 | 10/2012 | Margalit et al. |
| 9,259,474 B2 | 2/2016 | Margalit et al. |
| 9,526,705 B2 | 12/2016 | Margalit et al. |
| 9,574,210 B2 * | 2/2017 | Peer .................. A61K 9/1272 |
| 2001/0008772 A1 | 7/2001 | Smith et al. |
| 2001/0031740 A1 | 10/2001 | Unger et al. |
| 2001/0038851 A1 | 11/2001 | Allen et al. |
| 2001/0044528 A1 | 11/2001 | Innis et al. |
| 2002/0012998 A1 | 1/2002 | Gonda et al. |
| 2002/0061849 A1 | 5/2002 | Nielsen et al. |
| 2002/0131995 A1 | 9/2002 | Francis, Jr. |
| 2003/0175733 A1 | 9/2003 | Kirst et al. |
| 2004/0241248 A1 | 12/2004 | Margalit et al. |
| 2006/0019912 A1 | 1/2006 | Burkoth et al. |
| 2009/0155178 A1 | 6/2009 | Margalit et al. |
| 2009/0291131 A1 | 11/2009 | MacLachlan et al. |
| 2009/0305409 A1 * | 12/2009 | Kogure .................. C12N 15/88 435/375 |
| 2012/0129916 A1 | 5/2012 | Peer et al. |
| 2013/0095032 A1 | 4/2013 | Margalit et al. |
| 2013/0303587 A1 * | 11/2013 | Yaworski ............. A61K 9/1075 514/44 A |
| 2015/0140108 A1 | 5/2015 | Peer et al. |
| 2015/0216998 A1 | 8/2015 | Feinstein et al. |
| 2016/0113882 A1 | 4/2016 | Margalit et al. |

FOREIGN PATENT DOCUMENTS

| | | |
|---|---|---|
| JP | 2003-528131 A | 9/2003 |
| JP | 2011-507534 A | 3/2011 |
| KR | 10-0806088 B1 | 2/2008 |
| WO | WO 2001/039815 A2 | 6/2001 |
| WO | WO 2003/015755 A1 | 2/2003 |
| WO | 2007/132873 | 11/2007 |
| WO | WO 2007/127219 A2 | 11/2007 |
| WO | WO 2007/127272 A2 | 11/2007 |
| WO | WO 2009/020270 A1 | 2/2009 |
| WO | WO 2009/026328 A2 | 2/2009 |
| WO | WO 2011/013130 A2 | 2/2011 |
| WO | WO 2011/075656 A1 | 6/2011 |
| WO | WO 2013/156989 A1 | 10/2013 |
| WO | WO 2015/198326 A1 | 12/2015 |

OTHER PUBLICATIONS

International Search Report and Written Opinion for International Application No. PCT/IL2013/050238 dated Jun. 20, 2013, 10 pages.

International Preliminary Report on Patentability for International Application No. PCT/IL2013/050238 dated Oct. 21, 2014, 8 pages.

International Search Report and Written Opinion for International Application No. PCT/IL2015/050653 dated Oct. 15, 2015, 13 pages.

International Preliminary Report on Patentability for International Application No. PCT/IL2015/050653 dated Dec. 27, 2016, 8 pages.

Aoki et al., "In vivo transfer efficiency of antisense oligonucleotides into the myocardium using HVJ-liposome method." Biochem Biophys Res Commun (1997); 231(3): 540-545.

Barkay, Zahava, et al. "Three-dimensional characterization of drug-encapsulating particles using STEM detector in FEG-SEM." Micron (2009); 40(4): 480-485.

Bhargava et al., "Long double-stranded RNA-mediated RNA interference as a tool to achieve site-specific silencing of hypothalamic neuropeptides." Brain Res Brain Res Protoc (2004); 13(2): 115-125.

Billy, et al., "Specific interference with gene expression induced by long, double-stranded RNA in mouse embryonal teratocarcinoma cell lines", PNAS (2001); 98(25): 14428-14433.

Britannica Online Encyclopedia, "liposome", downloaded Nov. 14, 2008 http://www.britannica.com/Ebchecked/topic/342910/liposome, 1 page.

Brummelkamp et al., "A system for stable expression of short interfering RNAs in mammalian cells." Science (2002); 296 (5567): 550-553.

Castanotto et al., "Functional siRNA expression from transfected PCR products." RNA (2002); 8(11): 1454-1460.

Chekhonin, et al., "Immunoliposomal containers as systems of directed transport of minor interfering RNA into Schwann cells", Bulletin of Experimental Biology and Medicine (2008); 146(4): 451-454.

Choi et al., "Self-assembled hyaluronic acid nanoparticles for active tumor targeting." Biomaterials (2009); 31(1): 106-114.

Chono, et al., "An efficient and low immunostimulatory nanoparticle formulation for systemic siRNA delivery to the tumor", Journal of Controlled Release (2008); 131(1): 64-69.

Diallo et al., "Long endogenous dsRNAs can induce complete gene silencing in mammalian cells and primary cultures." Oligonucleotides (2003); 13(5): 381-392.

Dorland's Illustrated Medical Dictionary, "liposis", 30th edition, Saunders, PA, 2003, p. 1058, 3 pages.

Firth et al., "Studies on the use of antimitotic drugs entrapped within liposomes and of their action on a human glioma cell line," J Neurol Sci (1984); 63(2): 153-165.

Grishok et al., "Genes and mechanisms related to RNA interference regulate expression of the small temporal RNAs that control C.elegans developmental timing." Cell (2001); 106(1): 23-34.

Guo et al., "MicroRNA directs mRNA cleavage of the transcription factor NAC1 to downregulate auxin signals for *Arabidopsis* lateral root development." Plant Cell (2005); 17(5): 1376-1386.

(56) References Cited

OTHER PUBLICATIONS

Hammond et al., "Argonaute2, a link between genetic and biochemical analyses of RNAi." Science (2001); 293(5532): 1146-1150.
Han, et al., "Cationic derivatives of biocompatible hyaluronic acids for delivery of siRNA and antisense oligonucleotides", Journal of Drug Targeting (2009); 17(2): 123-132.
Herringson, et al., "Convenient targeting of stealth siRNA-lipoplexes to cells with chelator lipid-anchored molecules", Journal of Controlled Release (2009); 139(3): 229-238.
https://www.caymanchem.com/app/template/Product.vm/catalog/15084, retrieved from the internet on Apr. 19, 2015, 2 pages.
Huang, Chin-Yi, et al. "Lipitoids—novel cationic lipids for cellular delivery of plasmid DNA in vitro." Chemistry & Biology (1998); 5(6): 345-354.
Hutvágner and Zamore, "A microRNA in a multiple-turnover RNAi enzyme complex." Science (2002); 297(5589): 2056-2060.
Hutvágner et al., "A cellular function for the RNA-interference enzyme Dicer in the maturation of the let-7 small temporal RNA." Science (2001); 293(5531): 834-838.
Jiang, et al., "Hyaluronic acid-polyethyleneimine conjugate for target specific intracellular delivery of siRNA", Biopolymers (2008); 89(7): 635-642.
Jiang, et al., "Target Specific Intracellular Delivery of siRNA/PEI-HA Complex by Receptor Mediated Endocytosis", Molecular Pharmaceutics (2009); 6(3): 727-737.
Ketting et al., "Dicer functions in RNA interference and in synthesis of small RNA involved in developmental timing in C.elegans." Genes Dev (2001); 15(20): 2654-2659.
Kronenwett et al., "Oligodeoxyribonucleotide uptake in primary human hematopoietic cells is enhanced by cationic lipids and depends on the hematopoietic cell subset." Blood (1998); 91(3): 852-862.
Kundu et al., "Stability of lyophilized siRNA nanosome formulations." Int J Pharm (2012); 423(2): 525-534.
Landesman-Milo, D and Peer, D., "Toxicity profiling of several common RNAi-based nanomedicines: a comparative study." Drug Deliv. and Transl.Res. (2013); 4(1): 96-103 (published online May 29, 2013) DOI 10.1007/s13346-013-0158-7).
Lasic, Danilo D. "Liposomes", Liposomes in gene delivery, CRC press, 1997, Ch. 6, pp. 67-68.
Lavigne and Thierry, "Enhanced antisense inhibition of human immunodeficiency virus type 1 in cell cultures by DLS delivery system." Biochem Biophys Res Commun (1997); 237(3): 566-571.
Lee et al., "Target-specific intracellular delivery of siRNA using degradable hyaluronic acid nanogels." J Control Release (2007); 119(2): 245-252.
Lee et al., "The C.elegans heterochronic gene lin-4 encodes small RNAs with antisense complementarity to lin-14." Cell (1993); 75(5): 843-854.
Luft, "Making sense out of antisense oligodeoxynucleotide delivery: getting there is half the fun." J Mol Med (Berl) (1998); 76(2): 75-76.
Matveeva et al., "Prediction of antisense oligonucleotide efficacy by in vitro methods." Nat Biotechnol (1998); 16(13): 1374-1375.
Manjunath and Dykxhoorn, "Advances in synthetic siRNA delivery." Discovery Medicine (2010); 9(48): 418-430.
Merriam Webster Online Dictionary, "liposome", downloaded Nov. 14, 2008 http://www.merriam-webster.com/dictionary/liposome, 1 page.
Monsigny et al., "Sugar-lectin interactions: how does wheat-germ agglutinin bind sialoglycoconjugates?" Eur J Biochem (1980); 104(1): 147-153.
Mourelatos et al., "miRNPs: a novel class of ribonucleoproteins containing numerous microRNAs." Genes Dev (2002); 16(6): 720-728.
Nakajima, et al., "Mechanism of amide formation by carbodiimide for bioconjugation in aqueous media", Bioconjugate Chem. (1995); 6(1): 123-130.

O'Reilly, et al., "Endostatin: an endogenous inhibitor of angiogenesis and tumor growth", Cell (1997); 2(88): 277-285.
Paddison et al., "Stable suppression of gene expression by RNAi in mammalian cells." Proc Nall Acad Sci U S A (2002); 9(3): 1443-1448.
Parizotto et al., "In vivo investigation of the transcription, processing, endonucleolytic activity, and functional elevance of the spatial distribution of a plant miRNA." Genes Dev (2004); 18(18): 2237-2242 and erratum.
Peer, "Induction of therapeutic gene silencing in leukocyte-implicated diseases by targeted and stabilized nanoparticles: A mini-review." J Controlled Release (2010); 148(1): 63-68.
Peer, et al., "Systemic leukocyte-directed siRNA delivery revealing cyclin D1 as an anti-Inflammation target." Science (2008); 319(5863): 627-630.
Peer, et al., "Hyaluronan is a key component in cryoprotection and formulation of targeted unilamellar liposomes", Biochimica et Biophysica Acta (2003); 1612(1): 76-82.
Peer, et al., "Selective gene silencing in activated leukocytes by targeting siRNAs to the integrin lymphocyte function-associated antigen-1", PNAS (2007); 104(10): 4095-4100.
Peer, et al., "Physicochemical evaluation of a stability-driven approach to drug entrapment in regular and in surface-modified liposomes", Archives of Biochemistry and Biophysics (2000); 383(2): 185-190.
Peer, D and Shimaoka, M. "Systemic siRNA delivery to leukocyte-implicated diseases." Cell Cycle (2009); 8(6): 853-859.
Pierce 1994 Catalog, 4 pages.
Rajur et al., Covalent protein—Oligonucleotide conjugates for efficient delivery of antisense molecules. Bioconjug Chem (1997); 8(6): 935-940.
Rivkin, Ilia, et al. "Paclitaxel-clusters coated with hyaluronan as selective tumor-targeted nanovectors." Biomaterials (2010); 31(27): 7106-7114.
Romberg, Birgit, et al. "Enzyme-induced shedding of a poly (amino acid)-coating triggers contents release from dioleoyl phosphatidylethanolamine liposomes." International Journal of Pharmaceutics (2008); 355(1): 108-113.
Rose et al., "Functional polarity is introduced by Dicer processing of short substrate RNAs." Nucleic Acids Res (2005); 33(13): 4140-4156.
Ruozi, Barbara, et al. "Immunoliposomal systems targeting primary effusion lymphoma: in vitro study." Nanomedicine (2010); 5(7): 1051-1064.
Saul, Justin M., et al. "Controlled targeting of liposomal doxorubicin via the folate receptor in vitro." Journal of Controlled Release (2003); 92(1): 49-67.
Shinagawa and Ishii, "Generation of Ski-knockdown mice by expressing a long double-strand RNA from an RNA polymerase II promoter." Genes Dev (2003); 17(11): 1340-1345.
Strat et al., "Specific and nontoxic silencing in mammalian cells with expressed long dsRNAs." Nucleic Acids Res (2006); 34(13): 3803-3810.
Surace, et al., "Lipoplexes targeting the CD44 hyaluronic acid receptor for efficient transfection of breast cancer cells", Molecular Pharmaceutics (2009); 6(4): 1062-1073.
Taetz et al., "Hyaluronic acid-modified DOTAP/DOPE liposomes for the targeted delivery of anti-telomerase siRNA to CD44-expressing lung cancer cells." Oligonucleotides (2009); 19(2): 103-116.
Tam, Yuen Yi C., et al. "Advances in lipid nanoparticles for siRNA delivery." Pharmaceutics (2013); 5(3): 498-507.
Thermo Scientific Crosslinking Technical Handbook, Jan. 1, 2012, XP55272448; Retrieved from the Internet: URL: hllps://tools.thermofisher.com/contenl/sfs/brochures/1602163-Crosslinking-Reagents-Handbook.pdf; 56 pages.
Torchilin, Vladimir P. "Recent advances with liposomes as pharmaceutical carriers." Nature Reviews Drug Discovery (2005); 4(2): 145-160.
Tran et al., "Control of specific gene expression in mammalian cells by co-expression of long complementary RNAs." FEBS (2004); Lett 573(1-3): 127-134.
Tuschl, "RNA interference and small interfering RNAs." Chembiochem (2001); 2(4): 239-245.

(56) References Cited

OTHER PUBLICATIONS

Walton et al., "Prediction of antisense oligonucleotide binding affinity to a structured RNA target." Biotechnol Bioeng (1999); 65(1): 1-9.
Weinstein and Peer, "RNAi nanomedicines: challenges and opportunities within the immune system." Nanotechnology (2010); 21(23): 1-13.
Wightman et al., "Posttranscriptional regulation of the heterochronic gene lin-14 by lin-4 mediates temporal pattern formation in C. elegans." Cell (1993); 75(5): 855-862.
Williams and Rubin, ARGONAUTE1 is required for efficient RNA interference in *Drosophila* embryos. Proc Natl Acad Sci US A (2002); 99(10): 6889-6894.
Yagi et al., "Interferon-beta endogenously produced by intratumoral injection of cationic liposome-encapsulated gene: cytocidal effect on glioma transplanted into nude mouse brain," Biochem Mol Biol Int (1994); 32(1): 167-171.
Yen et al., "CD44 Mediated Nonviral Gene Delivery into Human Embryonic Stem Cells via Hyaluronic-Acid-Coated Nanoparticles." ACS Biomater Sci Eng (2016); 2(3): 326-335.
Yu, et al., "let-7 regulates self renewal and tumorigenicity of breast cancer cells", Cell (2007); 131(6): 1109-1123.
Zeng et al., "Both natural and designed micro RNAs can inhibit the expression of cognate mRNAs when expressed in human cells." Mol Cell (2002); 9(6): 1327-1333.
Alberts et al., (2002) Molecular Biology of the Cell, 4th Edition, New York, Garland Science. ISBN-10:0-8153-3218-1 ISBN-10: 0-8153-4072-9; p. 587.
Cullis et al., (1986) Lipid polymorphism and the roles of lipids in membranes. Chem Phys Lipids 40(2-4): 127-144.
Jacoby et al., (2015) Metastability in lipid based particles exhibits temporally deterministic and controllable behavior. Scientific Reports 5: 9481; 7 pages.
Anonymous: "Lipid extruder", URL: http://www.transferra.ca/products/lipex-extruder/. 1 page, downloaded on May 17, 2018.

* cited by examiner

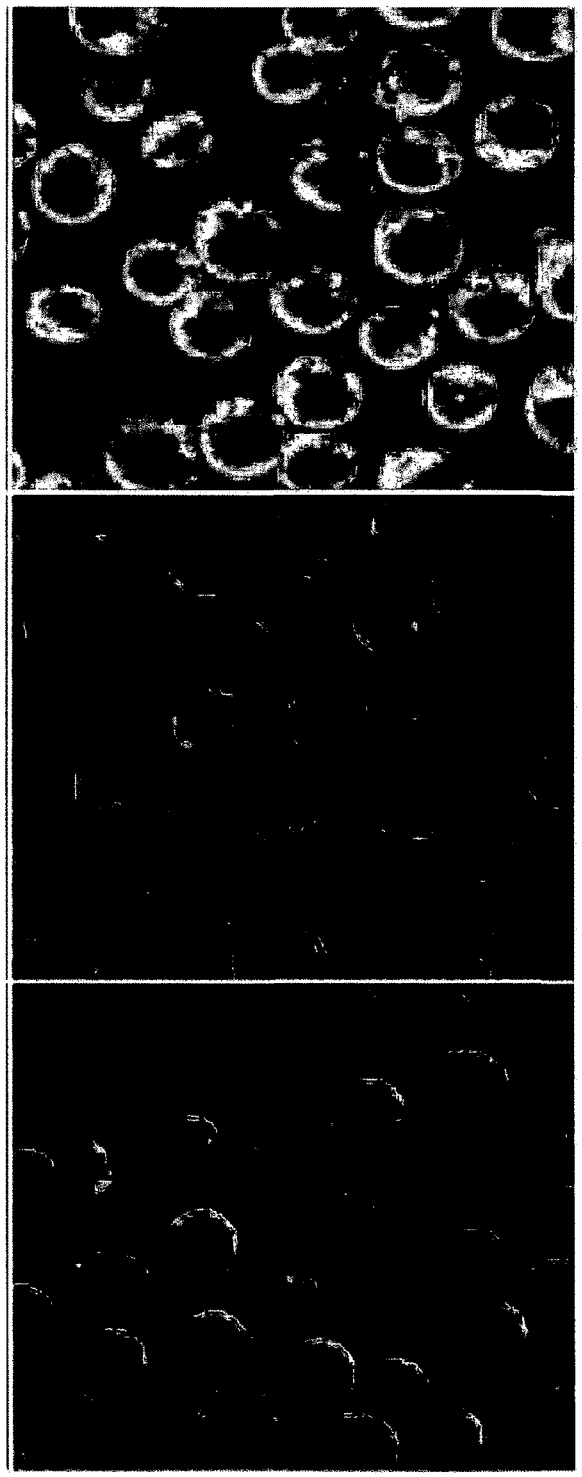

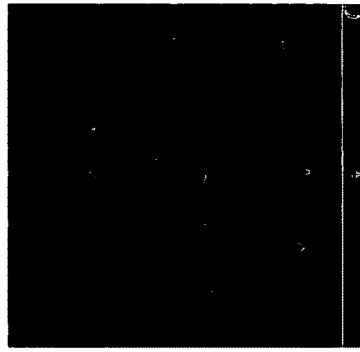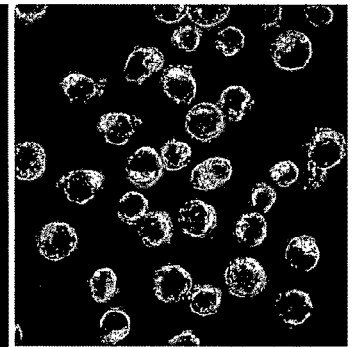
FIG. 9A Surface - Alexa 488 - labeled
FIG. 9B Cy3-siRNA
FIG. 9C DIC/Merge

CELL-TARGETING NANOPARTICLES COMPRISING POLYNUCLEOTIDE AGENTS AND USES THEREOF

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: QUIE_002_00US_SeqList_ST25.txt, date recorded: Nov. 1, 2016, file size 2 kilobytes).

FIELD AND BACKGROUND OF THE INVENTION

The present invention, in some embodiments thereof, relates to cell-targeting nanoparticles comprising polynucleotide agents and uses thereof.

Most cancers are not uniform and contain subpopulations of cells that are relatively resistant to chemo/radiotherapy. These cells are not eliminated by treatment and may be the source of cancer recurrence. One leading theory is that tumors are initiated by such rare drug-resistant cells within the tumor, called cancer stem cells or tumor-initiating cells (T-IC), which share properties with normal tissue stem cells. These cells can self renew and can be passaged indefinitely both in vitro and in vivo and can differentiate into multiple cell lineages. Importantly, they are much more malignant than the bulk of tumor cells in immunodeficient mice, forming tumors with many fewer cells, and frequently the tumors are more metastatic.

One common feature of all T-IC is a high expression of CD44 named ($CD44^{high}$), $CD44^{high}$ with or without several other markers (such as CD133, $CD24^{low}$ or $CD24^+$, CD166 and EpCAM) is found in blood and solid tumors, among them breast, pancreatic, leukemia, brain and melanoma.

Most cancer stem cells are relatively drug resistant and more malignant than the bulk of tumor cells. Therefore it is imperative to develop therapies that address this subpopulation in order to treat different type of cancer stem cells successfully.

Although it is only recently that RNA interference (RNAi) was shown in mammals, the prospect of harnessing RNAi for human therapy has developed rapidly. Phase I and II clinical studies using siRNAs to treat macular degeneration and respiratory syncytial virus infection have been encouraging.

However, many of these promising therapies were performed by locally injecting siRNAs into a xenotransplanted tumor. The greatest obstacle for harnessing RNAi for cancer therapy is systemically delivering siRNAs to silence gene expression not only in a primary tumor, but also in occult metastases and disseminated disease.

Particles have been developed that systemically target leukocytes. Such particles were formed by mixing siRNAs with a fusion protein composed of a cell targeting moiety (antibody fragment or cell surface receptor ligand against an internalizing leukocyte integrin) and an RNA binding peptide such as protamine [Peer et al., Proceedings of the National Academy of Sciences of the United States of America 104, 4095-4100 (2007)]. Intravenous injection of siRNA fusion protein nanoparticles specifically target and inhibit pulmonary hematopoietic cell tumors. In addition, it has been shown that lipid-based nanoparticles decorated with anti-integrin antibody can selectively deliver siRNAs to leukocytes involved in gut inflammation [Peer et al., Science 319, 627-630 (2008)]. This platform can be used to target different cell surface receptors by changing the antibodies decorating the particle's surface. However, this is a sophisticated strategy that cannot address the ability to target cancer stem cells.

International Application WO2009/020270 and Jiang et al [Biopolymers, Vol. 89, No. 7, 2008] teach a delivery system for nucleic acids using a composition comprising polyethyleneimine and hyaluronic acid. The composition is generated at a pH above 4.5. The particles generated had a zeta potential of 3.6, 13.2 and 24.9 with a size of 21 nm.

Taetz et al. [Oligonucleotides, Vol. 19, No. 2, Epub April 2009] teaches reacting liposomes which have been previously attached to hyaluronic acid with siRNA to produce lipoplexes for the treatment of cancer. The size of the lipoplexes were between 100-200 nm with a zeta potential of about −40 mV.

Surace et al [Molecular Pharmaceutics, Vol. 6, No. 4, pages 1062-73 teaches using liposomes previously attached to hyaluronic acid to form lipoplexes together with plasmid DNA. Lipoplexes displayed a negative zeta potential and a mean diameter between 250-300 nm.

Han Su-Eun et al [Journal of Drug Targeting, Vol. 17, No. 2, February 2009] teach a delivery system for nucleic acids using a composition comprising polyethyleneimine and hyaluronic acid. The composition is generated at a pH above 4.5. The particles generated had a zeta potential between 45-70 mV and are about 185 nm in diameter.

Herringson et al [Journal of Controlled Release, Vol. 139, No. 3, pages 229-238] teaches encapsulation of siRNA into neutral stealth liposomes and engraftment with CD4 ligand. The liposomes had a mean diameter of 243 nm and a zeta potential of −11.5 mV and −1.5 mV.

Chono et al., Journal of Controlled Release, Volume 131, Issue 1, 6 Oct. 2008, Pages 64-69, teaches nanoparticle formulation comprising liposomes, protamine and hyaluronic acid for systemically delivering siRNA into a tumor.

Additional background art includes U.S. Pat. No. 7,544,374 and U.S. Patent Application No. 20090155178 which teaches non-homogeneous populations of particles of lipidated glycosaminoglycans as gene delivery materials.

SUMMARY OF THE INVENTION

According to an aspect of some embodiments of the present invention there is provided a method of generating a particle, the particle being for delivery of a polynucleotide to a target cell, the method comprising:

(a) contacting the polynucleotide with a composition comprising cationic molecules, wherein the cationic molecules condense the polynucleotide by electrostatic interactions to generate a complex, wherein the cationic molecules are not comprised in a liposome; and (b) covalently binding the complex to a targeting moiety at a pH equal to or below about 4.5, thereby generating the particle for delivery of the polynucleotide agent to the target cell.

According to an aspect of some embodiments of the present invention there is provided a particle generated according to any of the methods of the present invention.

According to an aspect of some embodiments of the present invention there is provided a composition comprising a plurality of the particles of the present invention.

According to an aspect of some embodiments of the present invention there is provided a composition comprising a substantially homogeneous population of particles, the particles comprising a core of siRNA and cationic molecules and a shell comprising targeting moieties, wherein each of the particles of the population of particles comprises a zeta potential of about −40 mV and wherein each of the particles of the population of particles is about 100-300 nm in diameter when in solution.

According to an aspect of some embodiments of the present invention there is provided a composition comprising a substantially homogeneous population of particles, the particles comprising a core of miRNA and cationic molecules, and a shell comprising targeting moieties, wherein each of the particles of the population of particles is about 30-50 nm in diameter when in solution.

According to an aspect of some embodiments of the present invention there is provided a method of down-regulating a gene of interest in a target cell, the method comprising contacting particles with the target cell, wherein the particles are generated according to the method of the present invention and the target cell expresses CD44, thereby down-regulating a gene of interest in a target cell.

According to an aspect of some embodiments of the present invention there is provided a method of treating cancer in a subject in need thereof, the method comprising administering to the subject a therapeutically effective amount of particles, the particles being generated according to the method of the present invention, thereby treating the cancer.

According to some embodiments of the invention, the polynucleotide comprises DNA.

According to some embodiments of the invention, the polynucleotide comprises RNA.

According to some embodiments of the invention, the polynucleotide is single stranded.

According to some embodiments of the invention, the polynucleotide is double stranded.

According to some embodiments of the invention, the polynucleotide comprises an RNA silencing agent.

According to some embodiments of the invention, the RNA silencing agent is selected from the group consisting of an siRNA, a miRNA, an antisense oligonucleotide and a ribozyme.

According to some embodiments of the invention, the RNA silencing agent comprises an siRNA or miRNA.

According to some embodiments of the invention, the cationic molecule is selected from the group consisting of a cationic polypeptide, a cationic lipid, a cationic surfactant and a synthetic polymer.

According to some embodiments of the invention, the cationic lipid is selected from the group consisting of 1,2-Dilauroyl-sn-Glicero-3-Phosphoethanolamine (DLPE) and 1,2-Dilauroyl-sn-Glicero-3-Phosphorylglycerol (DLPG), dioleoyl-1,2-diacyl-3-trimethylammonium-propane (DOTAP, at 18:1; 14:0; 16:0, 18:0) and N-[1-(2,3-dioleyloxy)propyl]-N,N,N-trimethlylammonium chloride (DOTMA); dimethyldioctadecylammonium (DDAB); 1,2-dilauroyl-sn-glycero-3-ethylphosphocholine (Ethyl PC, at 12:0; 14:0; 16:0; 18:0; 18:1; 16:0-18:1); 1,2-di-(9Z-octadecenoyl)-3-dimethylammonium-propane and 3β-[N-(N',N'-dimethylaminoethane)-carbamoyl]cholesterol hydrochloride (DC-Cholesterol).

According to some embodiments of the invention, the composition further comprises a neutral lipid.

According to some embodiments of the invention, the neutral lipid comprises dioleilphosphatidylethanolamine (DOPE).

According to some embodiments of the invention, the composition further comprises anionic phospholipids.

According to some embodiments of the invention, the anionic phospholipids are selected from the group consisting of phosphatidylserine, phosphatidic acid, phosphatidylcholine and phosphatidyl glycerol.

According to some embodiments of the invention, the composition further comprises cholesterol.

According to some embodiments of the invention, the synthetic polymer comprises polyethylenimine (PEI)-or poly-L-lysine.

According to some embodiments of the invention, the targeting moiety comprises a polypeptide targeting moiety.

According to some embodiments of the invention, the targeting moiety is selected from the group consisting of an antibody, an antibody fragment, an aptamer and a receptor ligand.

According to some embodiments of the invention, the targeting moiety comprises a glycosaminoglycan.

According to some embodiments of the invention, the glycosaminoglycan is selected from the group consisting of hyaluronic acid (HA), keratan sulfate, chondroitin sulfate, heparin sulfate, heparan sulfate, dermatin sulfate, salts, and mixtures thereof.

According to some embodiments of the invention, the glycosaminoglycan comprises HA.

According to some embodiments of the invention, the method further comprises activating the glycosaminoglycan prior to step (b).

According to some embodiments of the invention, the activating is effected by incubating the glycosaminoglycan in an acidic buffer.

According to some embodiments of the invention, the composition comprises hydrogenated phosphatidylcholine (HSPC), cholesterol and dioleoyl trimethylammonium propane (DOTAP).

According to some embodiments of the invention, the composition comprises (1,2-Dilauroyl-sn-Glicero-3-Phosphoethanolamine (DLPE) and 1,2-Dilauroyl-sn-Glicero-3-Phosphorylglycerol (DLPG).

According to some embodiments of the invention, the targeting moiety comprises HA and the polynucleotide agent comprises an siRNA or miRNA.

According to some embodiments of the invention, the complex is not extruded prior to step (b).

According to some embodiments of the invention, the particle is about 100 nm in diameter when dried on a silicon surface.

According to some embodiments of the invention, the particle is about 30 nm in diameter when dried on a silicon surface.

According to some embodiments of the invention, the particle is between about 30-300 nm in diameter in solution.

According to some embodiments of the invention, the particle is round in shape.

According to some embodiments of the invention, the particle comprises a zeta potential of about −40 mV.

According to some embodiments of the invention, the particle is charged.

According to some embodiments of the invention, the particle is neutral.

According to some embodiments of the invention, the particle is a nanoparticle.

According to some embodiments of the invention, the targeting moiety comprises HA.

According to some embodiments of the invention, the particle further comprises at least one additional targeting moiety, the additional targeting moiety being selected from the group consisting of an antibody, an antibody fragment, a receptor ligand and an aptamer.

According to some embodiments of the invention, the particle comprises more than about 6,000 siRNA or miRNA molecules.

According to some embodiments of the invention, the composition is substantially homogeneous.

According to some embodiments of the invention, the administering is effected in vivo.

According to some embodiments of the invention, the administering is effected ex vivo.

According to some embodiments of the invention, the RNA silencing agent is selected to down-regulate expression of an oncogene.

According to some embodiments of the invention, the RNA silencing agent is selected to down-regulate expression of a gene associated with viability.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1A: Particles made out of DOTAP with HA in acetate buffer (AB) surface topography.

The H-mers topography was imaged by environmental scanning electron microscopy (E-SEM). Particles have a discrete globular shape, and sizes are around 100 nm in diameter, when dried on silicon surfaces. FIG. 1B: Particles made from DOTAP with HA in DDW (double distilled water have an undefined structure and do not have discrete shapes. There is a core particle surrounded by sheets of fibers.

FIGS. 8A-C are photographs illustrating selective siRNA delivery to human leukemia stem cells using particles of the present invention. FIG. 8A—siRNA alone; FIG. 8B—oligofectamine™; FIG. 8C; particle according to embodiments of the present invention.

FIGS. 9A-C are images illustrating that particles according to embodiments of the present invention are capable of delivering siRNAs to human AML primary cells.

DESCRIPTION OF SPECIFIC EMBODIMENTS OF THE INVENTION

The present invention, in some embodiments thereof, relates to cell-targeting nanoparticles comprising polynucleotide agents, methods of generating same and uses thereof.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Tumor initiating cells (T-IC) or cancer stem cells, which highly express the surface receptor CD44, are believed to be a major cause for cancer recurrence and are highly chemo and radiation resistant. There is a need to develop a strategy to deliver drugs (among them novel class of inhibitors such as siRNAs or miRNAs mimetic) that can selectively target all types of cancer cells (including cancer stem cells). The present inventors have devised a strategy that utilizes the interaction between CD44 to its ligand, hyaluronan (HA), by generating nanoparticles (also termed hyalumers or H-mers), and show that they can be used to selectively deliver siRNAs into T-IC, inducing potent gene silencing which can lead to the eradication of these cells.

The nanoparticles may be comprised of any cationic molecule provided they are capable of condensing the polynucleotide by a charge-charge interaction.

The present inventor has found that crosslinking of the targeting moiety (e.g. Hyaluronan; HA) to the cationic molecules at a pH below 4.5 generated nanoparticles that were more uniform and that could entrap larger amounts of polynucleotide agents than if the crosslinking was performed at higher pHs. The method of generating the particles was effected essentially in one step—i.e. without the need for further energy to down-size the particles following addition of the polynucleotide agent and prior to crosslinking with the targeting moiety—e.g. without generation of liposomes.

Figure 1A:
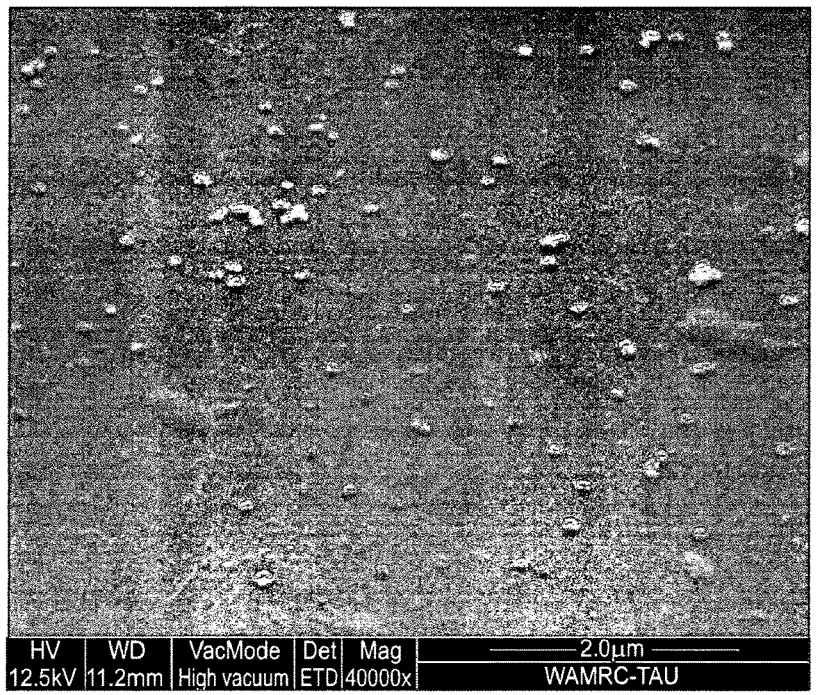
FIGS. 1A-B are photographs illustrating the surface topography of particles of embodiments of the invention.
Figure 1B:
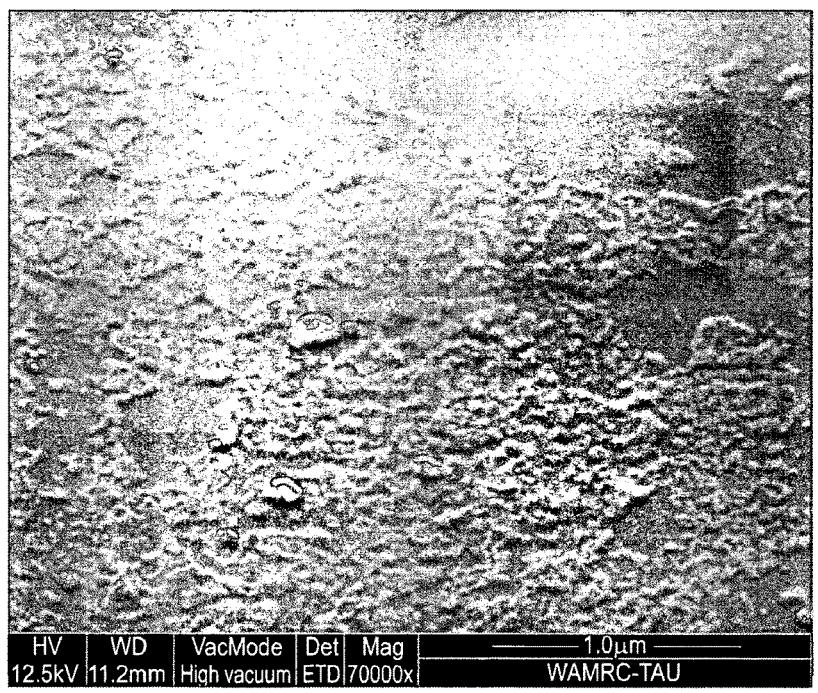
Figure 2B:
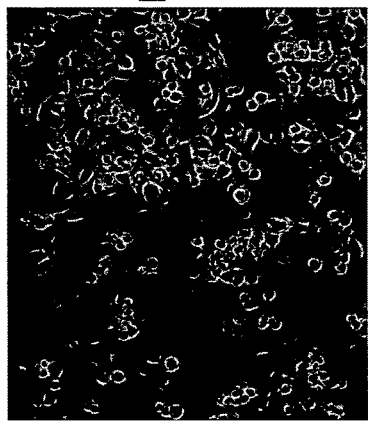
FIGS. 2A-F are photographs illustrating transfection of Cy3-siRNAs with particles generated according to embodiments of the present invention in AB (FIGS. 2B, 2D and 2F) or DDW (FIGS. 2A, 2C and 2E) in PANC-1 (human pancreatic adenocarcinoma).
Figure 2D:
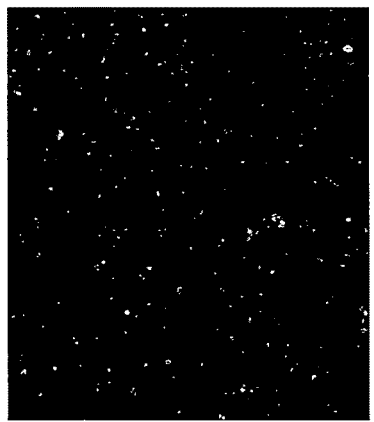
Figure 2F:
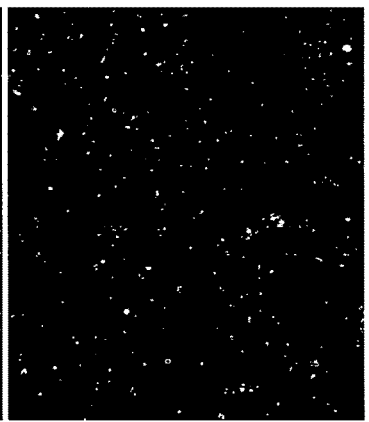
Figure 2A:
Figure 2C:
Figure 2E:
Figure 3:
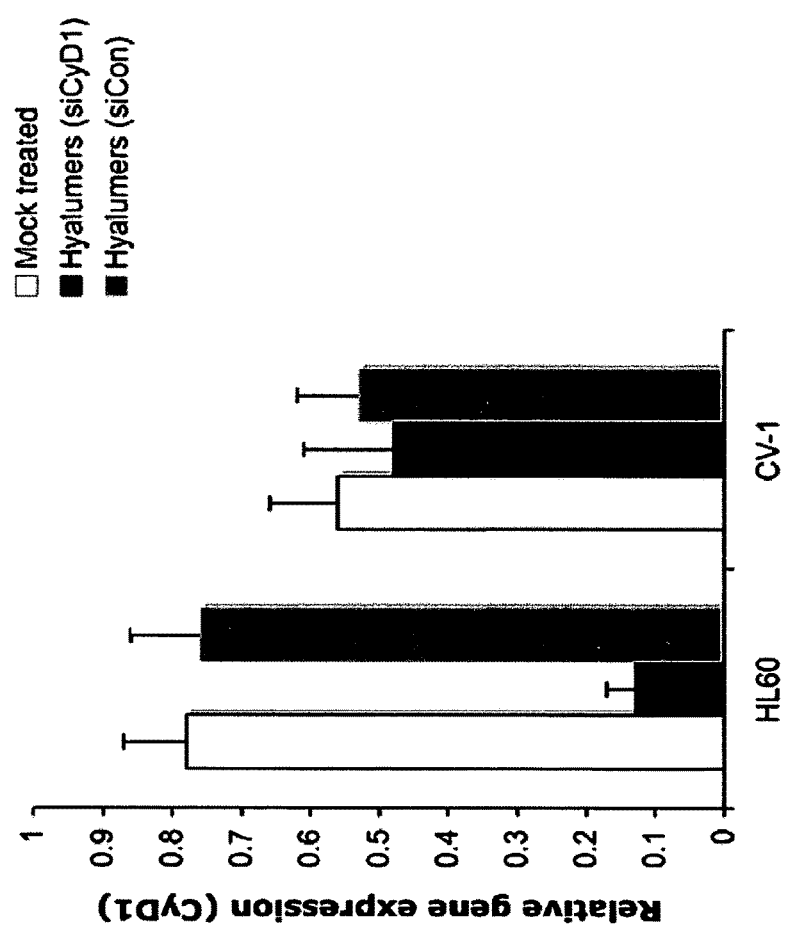
FIG. 3 is a bar graph illustrating selective knockdown of CyD1 in leukemic stem cells using particles of embodiments of the present invention.
Figure 4:
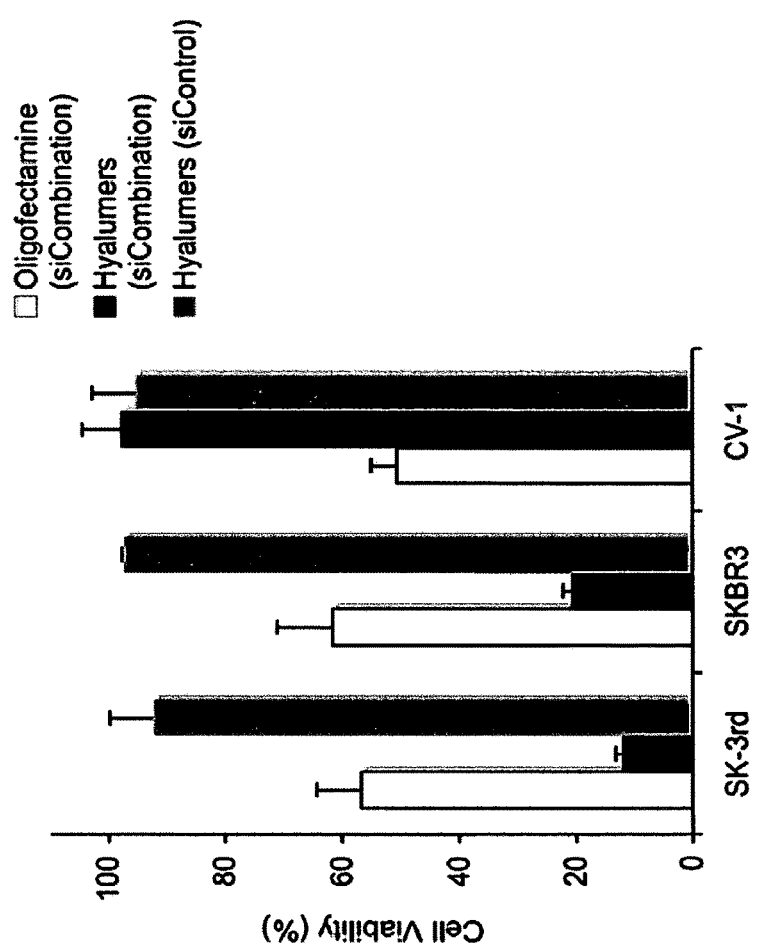
FIG. 4 is a bar graph illustrating eradication of cancer stem cells using a mixture of siRNAs against oncogenes delivered via particles of embodiments of the present invention.
Figure 5:
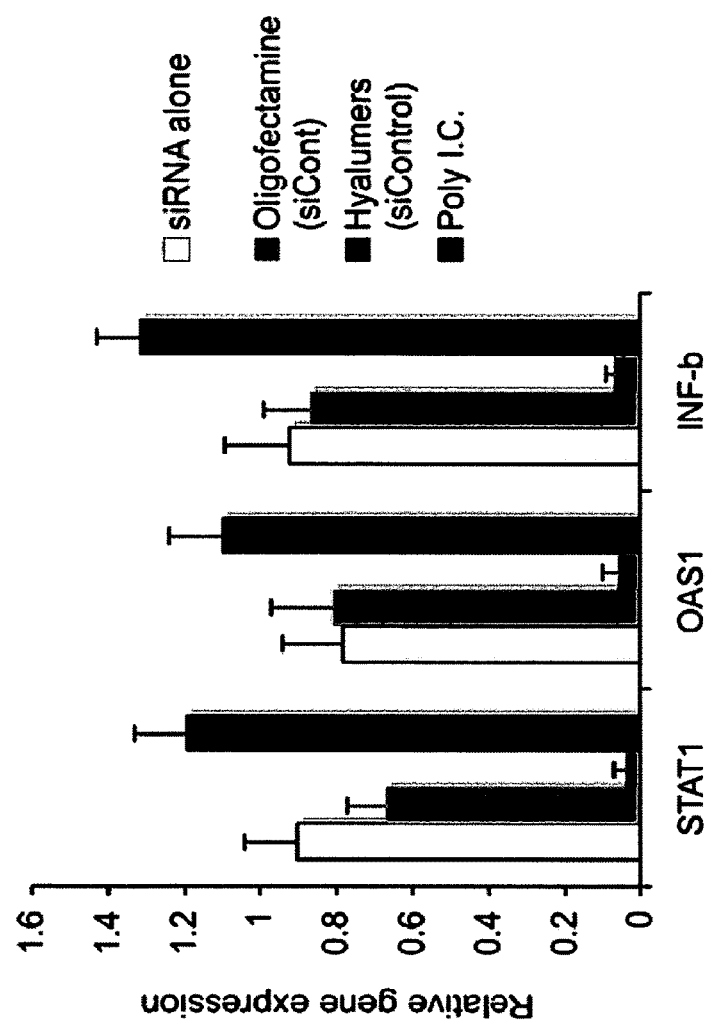
FIG. 5 is a bar graph illustrating that particles of embodiments of the present invention entrapping siRNAs do not induce interferon responses.
Figure 6:
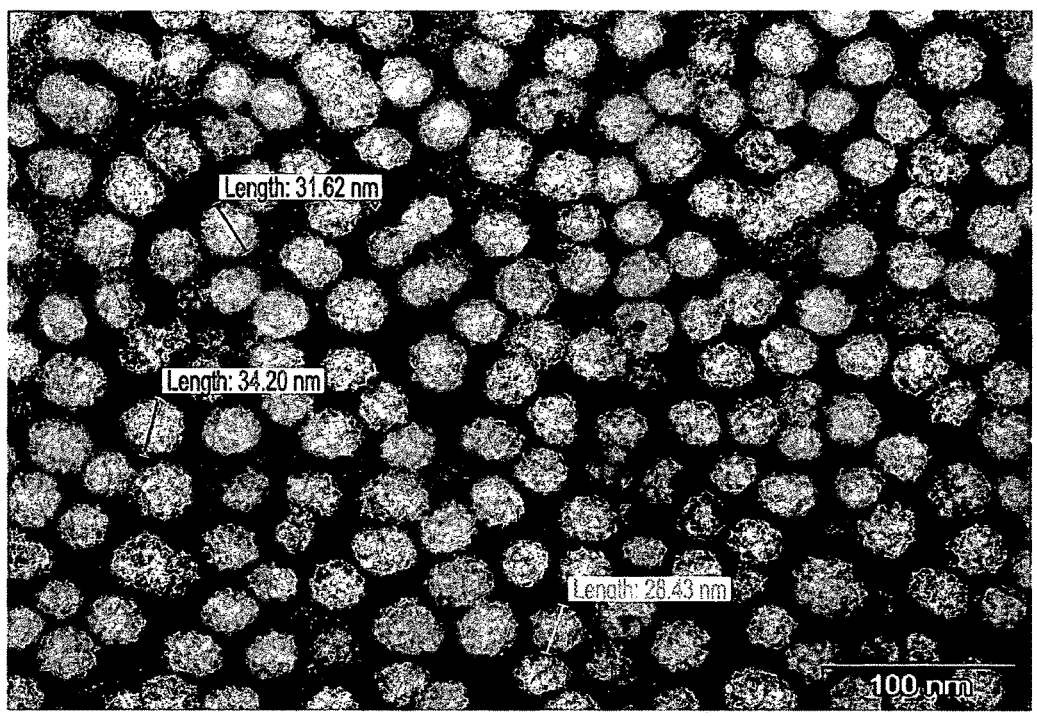
FIG. 6 is an image of particles according to embodiments of the present invention entrapping miRNAs.
Figure 7:
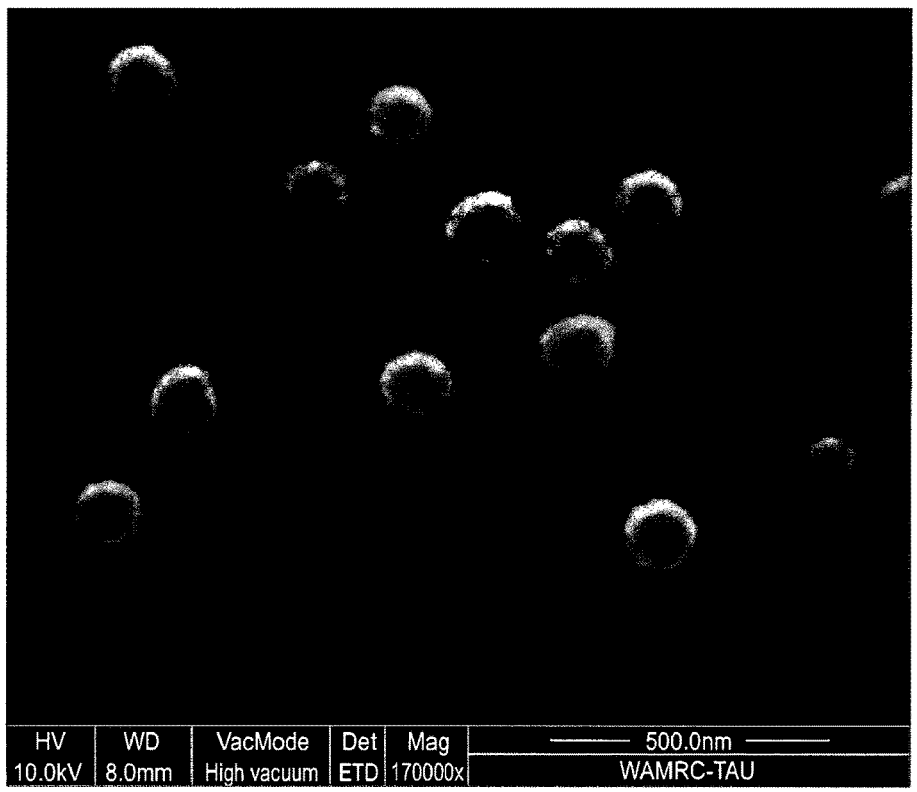
FIG. 7 is a photograph illustrating surface topography of particles of embodiments of the present invention as imaged by environmental scanning electron microscopy (E-SEM). Particles have a globular shape, and sizes are around 100 nm in diameter, when dried on silicon surfaces.
Figure 10:
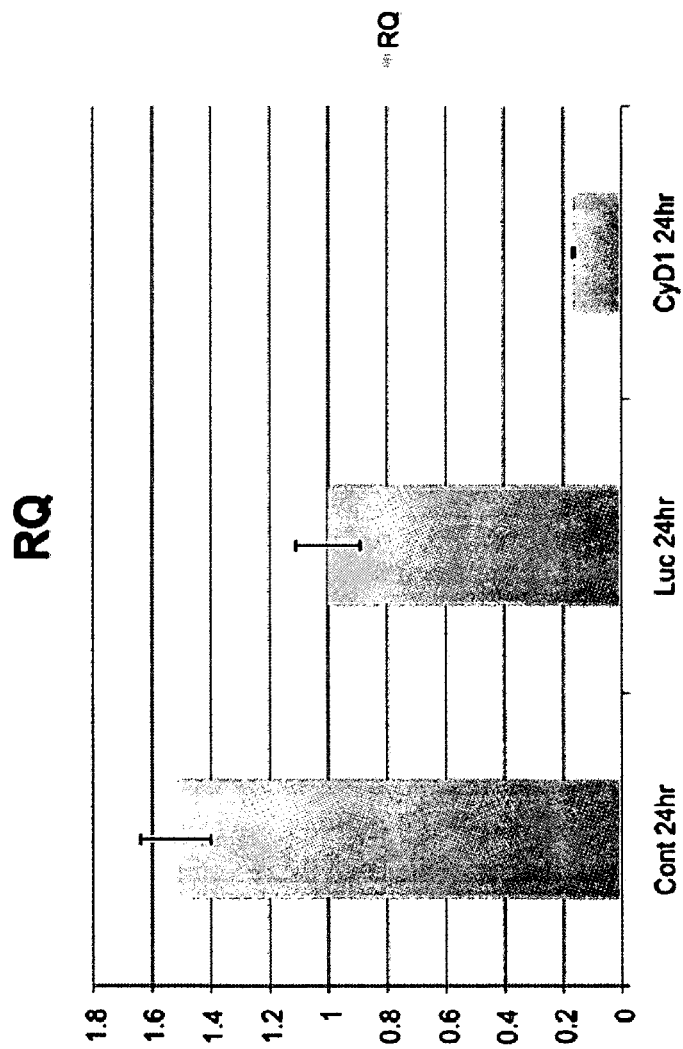
FIG. 10 is a bar graph illustrating that Cyclin D1-siRNA (50 nM) delivered via particles according to embodiments of the present invention induced potent gene silencing in human primary AML cells.

Accordingly the populations of polynucleotide agent-encapsulated nanoparticles generated by the present inventor were shown to be highly homogeneous (FIGS. 1A, 6 and 7). The particles of the present invention were also shown to selectively deliver their polynucleotide load to cells having the CD44 surface receptor (FIGS. 3 and 4). The particles of the present invention are protected from serum degradation and are therefore useful for in vivo therapy. In addition, the present inventor has shown that the polynucleotide agent-encapsulated nanoparticles do not induce interferon response—a prerequisite for safe and efficient delivery vehicle for systemic siRNA applications (FIG. 5).

Thus, according to one aspect of the present invention there is provided a method of generating a nanoparticle for delivery of a polynucleotide to a target cell, the method comprising:

(a) contacting the polynucleotide agent with a composition comprising cationic molecules, wherein the cationic molecules condense the polynucleotide agent by electrostatic interaction to generate a complex, wherein the cationic molecules are not comprised in a liposome; and (b) covalently binding the complex to a targeting moiety at a pH below about 4.5, thereby generating the nanoparticle for delivery of the polynucleotide agent to the target cell.

According to one embodiment, the acidic pH at which the covalent binding is effected is about 4.5, 4, 3.5, 3, 2.5 or below.

As used herein, the phrase "cationic molecules" refers to cationic polymers, cationic lipids, cationic surfactants and cationic polypeptides. According to this aspect of the present invention, the cationic molecules are not in the form of liposomes.

Exemplary cationic lipids include, but are not limited to 1,2-Dilauroyl-sn-Glicero-3-Phosphoethanolamine (DLPE) and 1,2-Dilauroyl-sn-Glicero-3-Phosphorylglycerol (DLPG), dioleoyl-1,2- diacyl-3-trimethylammonium-propane (DOTAP, at 18:1; 14:0; 16:0, 18:0) and N-[1-(2,3-dioleyloxy)propyl]-N,N,N-trimethlylammonium chloride (DOTMA); dimethyldioctadecylammonium (DDAB); 1,2-dilauroyl-sn-glycero-3-ethylphosphocholine (Ethyl PC, at 12:0; 14:0; 16:0; 18:0; 18:1; 16:0-18:1); 1,2-di-(9Z-octadecenoyl)-3-dimethylammonium-propane and 3β-[N-(N',N'-dimethylaminoethane)-carbamoyl]cholesterol hydrochloride (DC-Cholesterol).

Exemplary cationic polymers include, but are not limited to polyethylenimine (PEI) and poly-L-lysine.

The cationic molecules used to generate the nanoparticles of the present invention may also comprise other non-cationic components as described herein below.

Of particular interest are cationic lipids used in conjunction with cholesterol. Such compounds, particularly dimethyl dioctadecyl ammonium bromide (DDAB) or DOTIM, preferably used 1:1 with cholesterol, can be formulated with polynucleotides to yield a complex with a relatively low in vivo toxicity. As such, cholesterol groups that have been suitably mixed with, or derivatized to, cationic groups are particularly well suited for the practice of the presently described invention.

The cationic component of a suitable cholesterol lipid can comprise any of a variety of chemical groups that retain a positive charge between pH 5 through pH 8 including, but not limited to, amino groups (or oligo or poly amines), e.g., spermine, spermidine, pentaethylenehexamine (PEHA), diethylene triamine, pentamethylenehexamine, pentapropylenehexamine, etc.), amide groups, amidine groups, positively charged amino acids (e.g., lysine, arginine, and histidine), imidazole groups, guanidinium groups, or mixtures and derivatives thereof. Additionally, cationic polymers of any of the above groups (linked by polysaccharide or other chemical linkers) have also proven useful in gene delivery and can be incorporated into the presently described lipid complexes. The cross-linking agents used to prepare such polymers are preferably biocompatible or biotolerable, and will generally comprise at least two chemical groups (i.e., the cross-linkers are bifunctional) that are each capable of forming a bond with a suitable chemical group on the cation. For the purposes of the present disclosure, the term biocompatible shall mean that the compound does not display significant toxicity or adverse immunological effects at the contemplated dosages, and the term biotolerable shall mean that the adverse biological consequences associated with a given compound can be managed by the appropriate dosaging regimen or counter-therapy. The linker groups can be homobifunctional (same chemical groups) or heterobifunctional (different chemical groups). Optionally, in order to facilitate the release of the vector from the complex, the chemical linkage formed between the linking group and the cationic moiety will preferably be hydrolyzable under physiological conditions (i.e., pH labile, or otherwise subject to breakage in the target cell). Additionally, the cross-linking agent can comprise a bond that is hydrolyzable under physiological conditions in between the linking groups.

Optionally, the cross-linking agent can be combined with an additional cross-linking agent that allows for the formation of branched polymers. By varying the ratio of the branching linking molecules to polymerizing cross-linker, cationic polymers are produced with a variety of chemical characteristics.

Where appropriate, any or a variety (i.e., mixture) of other "helper" lipid moieties can be added to the presently described lipid or polymer/polynucleotide delivery vehicles as necessary to provide complexes with the desired characteristics. As such, any of a number of well known phospholipids can be added including, but not limited to, disteroyl-phosphatidyl-glycerol (DSPG), hydrogenated soy, phosphatidyl choline, phosphatidylglycerol, phosphatidic acid, phosphatidylserine, phosphatidylinositol, phosphatidyl ethanolamine, sphingomyelin, mono-, di-, and triacylglycerols, ceramides, cerebrosides, phosphatidyl glycerol (HSPG), dioleoyl-phosphatidylcholine (DOPC), dilauroyl-phosphatidyl-ethano-lamine (DLPE), cardiolipin, and the like. Typically, helper or otherwise neutral lipid shall comprise between about 15 percent to about 70 percent of the lipid component of a polynucleotide delivery complex, preferably between about 15 and about 60 percent, more preferably between about 30 and 60 percent, and more typically at least about 60 percent, and specifically at least about 50 percent. Conversely, the percentage of cationic lipid will preferably constitute about 30 to about 70 percent of the net lipid component of the complex, more preferably about 40 to about 60 percent, and specifically about 50 percent.

An exemplary composition which comprises cationic molecules includes hydrogenated phosphatidylcholine (HSPC), cholesterol and dioleoyl trimethylammonium propane (DOTAP). Another exemplary composition comprising cationic molecules includes (1,2-Dilauroyl-sn-Glicero-3-Phosphoethanolamine (DLPE) and 1,2-Dilauroyl-sn-Glicero-3-Phosphorylglycerol (DLPG).

During assembly, the cationic molecules will generally be combined with the polynucleotide agent at a cation/phosphate ratio that has been optimized for a given application. Usually, the DNA phosphate:cation ratio will be between about 1:8 (.mu.g DNA:nmol cationic lipid), preferably between about 2:1 and about 1:16 for intravenous administration, and about 1:1 for i.p., or aerosol applications, and the like.

Since ion pairing plays a role in the formation of the cation/polynucleotide complexes, the pH during complex formation can be varied to optimize or stabilize the interaction of the specific components. For instance, where non-pH sensitive cationic lipids are used, a pH as low as about 5 can be preferred to complex a given polynucleotide (e.g., RNA) or other chemical agent which can be coincorporated with the polynucleotide. Additionally, where the polynucleotide (e.g., DNA) is not substantially sensitive to base hydrolysis, circumstances can dictate that a pH of up to about 10 be used during complex formation. Generally, a pH within the range of about 5 to about 9, and preferably about 7, will be maintained during complex formation and transfection.

Similarly, the concentration of salt (e.g., NaCl, KCl, $MgCl_2$ etc.) can be varied to optimize complex formation, or to enhance the efficiency of polynulcucleotide agent delivery and expression. Additionally, factors such as the temperature at which the cationic lipid is complexed to the polynucleotide agent can be varied to optimize the structural and functional attributes of the resulting complexes. Additionally, the osmolarity of solution in which the complexes are formed can be altered by adjusting salt or other diluent concentration.

Since moderate concentrations of salt can impede complex formation, one can also adjust osmolarity by adding or substituting suitable excipients such as, but not limited to, glucose, sucrose, lactose, fructose, trehalose, maltose, mannose, and the like. The amount of sugar (dextrose, sucrose, etc., that can be present during complex formation shall generally vary from between about 2 percent and about 15 percent, preferably between about 3 percent and about 8 percent, and more preferably about 5 percent.

Alternatively, the osmolarity of the solution can also be adjusted by a mixture of salt and sugar, or other diluents including dextran 40, albumin, serum, lipoproteins, and the like. One skilled in the art would clearly know how to appropriately vary the concentration of salt and sugar to optimize the efficiency of gene delivery. Typical concentrations of salt and sugar that can serve as a starting point for further optimization are about 250 mM (glucose) and about 25 mM salt (NaCl). An additional feature of complex formation is temperature regulation. Typically, cationic lipids are complexed with polynucleotide at a temperature between about 4° C. and about 65° C., more typically between about 10° C. and about 42° C., preferably between about 15° C. and about 37° C. and more preferably at about room temperature. In many instances, precise regulation of temperature during complex formation (e.g., +/−1° C.) is important to minimize product variability.

The phrase "condense the polynucleotide" refers to decreasing the volume taken up by the polynucleotide. The present inventor has shown that a single nanoparticle generated according to embodiments of the present invention may incoroporation up to 6000 siRNA or miRNA molecules.

According to one embodiment, the polynucleotide is condensed such that it takes up 20% of its original volume, 30% of its original volume, 40% of its original volume, 50% of its original volume, 60% of its original volume, 70% of its original volume, 80% of its original volume or 90% of its original volume.

The polynucleotide agent in the complexes may include a DNA agent or an RNA agent. The polynucleotide may be single stranded or double stranded.

The disclosed methods may be used to deliver genes encoding antitumor agents to patients. For example, immune stimulants, tumor suppressor genes, or genes that hinder the growth, local extension, or metastatic spread of tumor cells can be delivered to tumor cells and other target cells, including, but not limited to, vascular endothelial cells and immune effector and regulator cells that subsequently express the genes to the detriment of the tumor. Particular examples of such genes include, but are not limited to: angiostatin, p53, GM-CSF, IL-2, G-CSF, BRCA1, BRCA2, RAD51, endostatin (O'Reilly et al., 1997, Cell, 88(2):277-285), TIMP 1, TIMP-2, Bcl-2, and BAX. Furthermore, similar methodologies can be employed to generate cancer vaccines similar to those disclosed in U.S. Pat. No. 5,637,483, issue to Dranoff et al., herein incorporated by reference.

According to another embodiment, the polynucleotide comprises an RNA silencing agent. In this context, it will be appreciated that the polynucleotide agent is selected depending on which gene of interest one wishes to down-regulate in the target cell.

According to one embodiment the RNA silencing agent is selected to down-regulate expression of an oncogene. According to another embodiment, the RNA silencing agent is selected to down-regulate expression of a gene associated with viability.

As used herein, the term "RNA silencing" refers to a group of sequence-specific regulatory mechanisms (e.g. RNA interference (RNAi), transcriptional gene silencing (TGS), post-transcriptional gene silencing (PTGS), quelling, co-suppression, and translational repression) mediated by RNA molecules which result in the inhibition or "silencing" of the expression of a corresponding protein-coding gene. RNA silencing has been observed in many types of organisms, including plants, animals, and fungi.

As used herein, the term "RNA silencing agent" refers to an RNA which is capable of inhibiting or "silencing" the expression of a target gene. In certain embodiments, the RNA silencing agent is capable of preventing complete processing (e.g., the full translation and/or expression) of an mRNA molecule through a post-transcriptional silencing mechanism. RNA silencing agents include noncoding RNA molecules, for example RNA duplexes comprising paired strands, as well as precursor RNAs from which such small non-coding RNAs can be generated. Exemplary RNA silencing agents include dsRNAs such as siRNAs, miRNAs and shRNAs. In one embodiment, the RNA silencing agent is capable of inducing RNA interference. In another embodiment, the RNA silencing agent is capable of mediating translational repression.

RNA interference refers to the process of sequence-specific post-transcriptional gene silencing in animals mediated by short interfering RNAs (siRNAs). The corresponding process in plants is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla. Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA.

The presence of long dsRNAs in cells stimulates the activity of a ribonuclease III enzyme referred to as dicer. Dicer is involved in the processing of the dsRNA into short pieces of dsRNA known as short interfering RNAs (siRNAs). Short interfering RNAs derived from dicer activity are typically about 21 to about 23 nucleotides in length and comprise about 19 base pair duplexes. The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex.

Accordingly, the present invention contemplates use of dsRNA to downregulate protein expression from mRNA.

According to one embodiment, the dsRNA is greater than 30 bp. The use of long dsRNAs (i.e. dsRNA greater than 30 bp) has been very limited owing to the belief that these longer regions of double stranded RNA will result in the induction of the interferon and PKR response. However, the use of long dsRNAs can provide numerous advantages in that the cell can select the optimal silencing sequence alleviating the need to test numerous siRNAs; long dsRNAs will allow for silencing libraries to have less complexity than would be necessary for siRNAs; and, perhaps most importantly, long dsRNA could prevent viral escape mutations when used as therapeutics.

Various studies demonstrate that long dsRNAs can be used to silence gene expression without inducing the stress response or causing significant off-target effects-see for example [Strat et al., Nucleic Acids Research, 2006, Vol. 34, No. 13 3803-3810; Bhargava A et al. Brain Res. Protoc. 2004;13:115-125; Diallo M., et al., Oligonucleotides. 2003; 13:381-392; Paddison P. J., et al., Proc. Natl Acad. Sci. USA. 2002;99:1443-1448; Tran N., et al., FEBS Lett. 2004;573: 127-134].

In particular, the present invention also contemplates introduction of long dsRNA (over 30 base transcripts) for gene silencing in cells where the interferon pathway is not activated (e.g. embryonic cells and oocytes) see for example Billy et al., PNAS 2001, Vol 98, pages 14428-14433. and Diallo et al, Oligonucleotides, Oct. 1, 2003, 13(5): 381-392. doi:10.1089/154545703322617069.

The present invention also contemplates introduction of long dsRNA specifically designed not to induce the interferon and PKR pathways for down-regulating gene expression. For example, Shinagwa and Ishii [Genes & Dev. 17 (11): 1340-1345, 2003] have developed a vector, named pDECAP, to express long double-strand RNA from an RNA polymerase II (Pol II) promoter. Because the transcripts from pDECAP lack both the 5'-cap structure and the 3'-poly (A) tail that facilitate ds-RNA export to the cytoplasm, long ds-RNA from pDECAP does not induce the interferon response.

Another method of evading the interferon and PKR pathways in mammalian systems is by introduction of small inhibitory RNAs (siRNAs) either via transfection or endogenous expression.

The term "siRNA" refers to small inhibitory RNA duplexes (generally between 18-30 basepairs) that induce the RNA interference (RNAi) pathway. Typically, siRNAs are chemically synthesized as 21mers with a central 19 bp duplex region and symmetric 2-base 3'-overhangs on the termini, although it has been recently described that chemically synthesized RNA duplexes of 25-30 base length can have as much as a 100-fold increase in potency compared with 21mers at the same location. The observed increased potency obtained using longer RNAs in triggering RNAi is theorized to result from providing Dicer with a substrate (27mer) instead of a product (21mer) and that this improves the rate or efficiency of entry of the siRNA duplex into RISC.

It has been found that position of the 3'-overhang influences potency of an siRNA and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript.

The strands of a double-stranded interfering RNA (e.g., an siRNA) may be connected to form a hairpin or stem-loop structure (e.g., an shRNA). Thus, as mentioned the RNA silencing agent of the present invention may also be a short hairpin RNA (shRNA).

The term "shRNA", as used refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. Examples of oligonucleotide sequences that can be used to form the loop include 5'-UUCAAGAGA-3' (Brummelkamp, T. R. et al. (2002) Science 296: 550) and 5'-UUUGUGUAG-3' (Castanotto, D. et al. (2002) RNA 8:1454). It will be recognized by one of skill in the art that the resulting single chain oligonucleotide forms a stem-loop or hairpin structure comprising a double-stranded region capable of interacting with the RNAi machinery.

According to another embodiment the RNA silencing agent may be a miRNA. It will be appreciated that the term "miRNA" also encompasses modified miRNAs and miRNA mimetics (antagomirs).

miRNAs are small RNAs made from genes encoding primary transcripts of various sizes. They have been identified in both animals and plants. The primary transcript (termed the "pri-miRNA") is processed through various nucleolytic steps to a shorter precursor miRNA, or "pre-miRNA." The pre-miRNA is present in a folded form so that the final (mature) miRNA is present in a duplex, the =two strands being referred to as the miRNA (the strand that will eventually basepair with the target) The pre-miRNA is a substrate for a form of dicer that removes the miRNA duplex from the precursor, after which, similarly to siRNAs, the duplex can be taken into the RISC complex. It has been demonstrated that miRNAs can be transgenically expressed and be effective through expression of a precursor form, rather than the entire primary form (Parizotto et al. (2004) Genes & Development 18:2237-2242 and Guo et al. (2005) Plant Cell 17:1376-1386).

Unlike, siRNAs, miRNAs bind to transcript sequences with only partial complementarity (Zeng et al., 2002, Molec. Cell 9:1327-1333) and repress translation without affecting steady-state RNA levels (Lee et al., 1993, Cell 75:843-854; Wightman et al., 1993, Cell 75:855-862). Both miRNAs and siRNAs are processed by Dicer and associate with components of the RNA-induced silencing complex (Hutvagner et al., 2001, Science 293:834-838; Grishok et al., 2001, Cell 106: 23-34; Ketting et al., 2001, Genes Dev. 15:2654-2659; Williams et al., 2002, Proc. Natl. Acad. Sci. USA 99:6889-6894; Hammond et al., 2001, Science 293:1146-1150;

Mourlatos et al., 2002, Genes Dev. 16:720-728). A recent report (Hutvagner et al., 2002, Sciencexpress 297:2056-2060)hypothesizes that gene regulation through the miRNA pathway versus the siRNA pathway is determined solely by the degree of complementarity to the target transcript. It is speculated that siRNAs with only partial identity to the mRNA target will function in translational repression, similar to an miRNA, rather than triggering RNA degradation.

Synthesis of RNA silencing agents suitable for use with the present invention can be effected as follows. First, the mRNA sequence is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tuschl ChemBiochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (www.ambion.com/techlib/tn/91/912.html).

Second, potential target sites are compared to an appropriate genomic database (e.g., human, mouse, rat etc.) using any sequence alignment software, such as the BLAST software available from the NCBI server (www.ncbi.nlm.nih.gov/BLAST/). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

It will be appreciated that the RNA silencing agent of the present invention need not be limited to those molecules containing only RNA, but further encompasses chemically-modified nucleotides and non-nucleotides.

In some embodiments, the RNA silencing agent provided herein can be functionally associated with a cell-penetrating peptide." As used herein, a "cell-penetrating peptide" is a peptide that comprises a short (about 12-30 residues) amino acid sequence or functional motif that confers the energy-independent (i.e., non-endocytotic) translocation properties associated with transport of the membrane-permeable complex across the plasma and/or nuclear membranes of a cell. The cell-penetrating peptide used in the membrane-permeable complex of the present invention preferably comprises at least one non-functional cysteine residue, which is either free or derivatized to form a disulfide link with a double-stranded ribonucleic acid that has been modified for such linkage. Representative amino acid motifs conferring such properties are listed in U.S. Pat. No. 6,348,185, the contents of which are expressly incorporated herein by reference. The cell-penetrating peptides of the present invention preferably include, but are not limited to, penetratin, transportan, pIs1, TAT(48-60), pVEC, MTS, and MAP.

mRNAs to be targeted using RNA silencing agents include, but are not limited to, those whose expression is correlated with an undesired phenotypic trait. Exemplary mRNAs that may be targeted are those that encode truncated proteins i.e. comprise deletions. Accordingly the RNA silencing agent of the present invention may be targeted to a bridging region on either side of the deletion. Introduction of such RNA silencing agents into a cell would cause a down-regulation of the mutated protein while leaving the non-mutated protein unaffected.

Thus, genes relating to cancer, rheumatoid arthritis and viruses might be targeted. Cancer-related genes include oncogenes (e.g., K-ras, c-myc, bcr/abl, c-myb, c-fms, c-fos and cerb-B), growth factor genes (e.g., genes encoding epidermal growth factor and its receptor, fibroblast growth factor-binding protein), matrix metalloproteinase genes (e.g., the gene encoding MMP-9), adhesion-molecule genes (e.g., the gene encoding VLA-6 integrin), tumor suppressor genes (e.g., bcl-2 and bcl-X1), angiogenesis genes, and metastatic genes. Rheumatoid arthritis-related genes include, for example, genes encoding stromelysin and tumor necrosis factor. Viral genes include human papilloma virus genes (related, for example, to cervical cancer), hepatitis B and C genes, and cytomegalovirus (CMV) genes (related, for example, to retinitis). Numerous other genes relating to these diseases or others might also be targeted.

Design of antisense molecules which can be used to efficiently downregulate a gene of interest must be effected while considering two aspects important to the antisense approach. The first aspect is delivery of the oligonucleotide into the cytoplasm of the appropriate cells, while the second aspect is design of an oligonucleotide which specifically binds the designated mRNA within cells in a way which inhibits translation thereof.

The prior art teaches of a number of delivery strategies which can be used to efficiently deliver oligonucleotides into a wide variety of cell types [see, for example, Luft J Mol Med 76: 75-6 (1998); Kronenwett et al. Blood 91: 852-62 (1998); Rajur et al. Bioconjug Chem 8: 935-40 (1997); Lavigne et al. Biochem Biophys Res Commun 237: 566-71 (1997); Aoki et al. (1997) Biochem Biophys Res Commun 231: 540-5 (1997) and Peer et al., Science 2008, 319(5863): 627-30.

In addition, algorithms for identifying those sequences with the highest predicted binding affinity for their target mRNA based on a thermodynamic cycle that accounts for the energetics of structural alterations in both the target mRNA and the oligonucleotide are also available [see, for example, Walton et al. Biotechnol Bioeng 65: 1-9 (1999)].

Such algorithms have been successfully used to implement an antisense approach in cells. For example, the algorithm developed by, Walton et al. enabled scientists to successfully design antisense oligonucleotides for rabbit beta-globin (RBG) and mouse tumor necrosis factor-alpha (TNF alpha) transcripts. The same research group has more recently reported that the antisense activity of rationally selected oligonucleotides against three model target mRNAs (human lactate dehydrogenase A and B and rat gp130) in cell culture as evaluated by a kinetic PCR technique proved effective in almost all cases, including tests against three different targets in two cell types with phosphodiester and phosphorothioate oligonucleotide chemistries.

In addition, several approaches for designing and predicting efficiency of specific oligonucleotides using an in vitro system were also published (Matveeva et al., Nature Biotechnology 16: 1374 - 1375 (1998)].

Since the presently described cationic lipid/polynucleotide or cationic polymer/polynucleotide complexes can be formulated into stable vesicles having a particular range of sizes, targeting agents can be attached (covalently bound) to the complexes in order to direct the complexes to specific cells and/or tissues. Accordingly, a targeting moiety or a combination of targeting moieties can be attached onto the complexes.

According to this aspect of the present invention, the targeting moiety is covalently bound under acidic conditions to the complex following complex formation or isolation. In this way, to the extent that the targeting agent is also capable of recognizing, or being recognized by, molecules on the cell surface, it can act as a bridge molecule which effectively places the complex in intimate contact with the cell surface.

The present inventor has found that addition of the targeting moiety (e.g. Hyaluronan; HA) to the cationic molecules at a pH below 4.5 generated nanoparticles that were more uniform and that could entrap larger amounts of polynucleotide agents than if the crosslinking was performed at higher pHs. According to one embodiment, the acidic pH at which the covalent binding is effected is about 4.5, 4, 3.5, 3, 2.5 or below.

For the purposes of the present disclosure, the term "targeting moiety" refers to any and all ligands or ligand receptors which can be incorporated into complexes. Such ligands can include, but are not limited to, antibodies such as IgM, IgG, IgA, IgD, and the like, or any portions or subsets thereof, cell factors, cell surface receptors such as, integrins, proteoglycans, sialic acid residues, etc., and ligands therefor, MHC or HLA markers, viral envelope proteins, peptides or small organic ligands, derivatives thereof, and the like. Of particular interest for targeted gene delivery applications are proteins encoding various cell surface markers and receptors. A brief list that is exemplary of such proteins includes, but is not limited to: CD1(a-c), CD4, CD8-11(a-c), CD15, CDw17, CD18, CD21-25, CD27, CD30-45(R(O, A, and B)), CD46-48, CDw49(b, d, f), CDw50, CD51, CD53-54, CDw60, CD61-64, CDw65, CD66-69, CDw70CD71, CD73-74, CDw75, CD76-77, LAMP-1 and LAMP-2, and the T-cell receptor, integrin receptors, endoglin for proliferative endothelium, or antibodies against the same.

According to a specific embodiment, the targeting moiety is a glycosaminoglycan, including, but not limited to hyaluronic acid (HA), keratan sulfate, chondroitin sulfate, heparin sulfate, heparan sulfate, dermatin sulfate, salts, and mixtures thereof.

In the case of glyscoaminoglycans, typically these molecules are activation prior to their incorporation into the nanoparitcles of the present invention. An exemplary method of activating the glycosaminoglycans is by incubating them in an acidic buffer as described in Examples 1 and 2.

In this manner, any of a variety of cells such as endothelial cells, stem cells, cancer stem cells, germ line cells, epithelial cells, islets, neurons or neural tissue, mesothelial cells, osteocytes, chondrocytes, hematopoietic cells, immune cells, cells of the major glands or organs (e.g., lung, heart, stomach, pancreas, kidney, skin, etc.), exocrine and/or endocrine cells, and the like, can be targeted for gene delivery.

Following attachment of the targeting moiety a suitable ligand or antibody, or mixture thereof, can be affixed to a suitable solid support, i.e., latex beads, microcarrier beads, membranes or filters, and the like, and used to selectively bind and isolate the nanoparticles that incorporate the targeting receptor or ligand from the remainder of the preparation. Thus, a method is provided for isolating the desired polynucleotide complexes prior to use.

As used herein, the term "nanoparticle" refers to a particle or particles having an intermediate size between individual atoms and macroscopic bulk solids. Generally, nanoparticle has a characteristic size (e.g., diameter for generally spherical nanoparticles, or length for generally elongated nanoparticles) in the sub-micrometer range, e.g., from about 1 nm to about 500 nm, or from about 1 nm to about 200 nm, or of the order of 10 nm, e.g., from about 1 nm to about 100 nm. Other exemplary sizes include from about 30 nm-250 nm or from 50 nm-300 nm.

Methods of measuring the size of the particles are known in the art and are further described in the Examples section herein below.

The nanoparticles may be of any shape, including, without limitation, elongated particle shapes, such as nanowires, or irregular shapes, in addition to more regular shapes, such as generally spherical, hexagonal and cubic nanoparticles. According to one embodiment, the nanoparticles are generally spherical.

Rounded particles are typically characterized quantitatively by a geometrical quantity known as sphericity, which generally quantifies the deviation of a particular geometrical shape from a perfect sphere.

Ideally, the sphericity of a three dimensional object is calculated by dividing the volume of the object to the volume of a sphere circumscribing the object. However, for some objects, the determination of the volume is difficult and oftentimes impossible. Therefore, for practical reasons, an alternative "two-dimensional" definition of sphericity is used. According to this alternative, the sphericity is defined as the ratio between the area of the projection of the object onto a certain reference plane and the area of a circle circumscribing the projection. For example, suppose that an image of the object is displayed on a planar display, then the planar display can be considered as a reference plane and the image of the object can be considered as the projection of the object on the reference plane.

Thus, denoting the area of the image by A and the perimeter of the image by P, the sphericity, s, can be defined as $s=4\pi A/P^2$. As will be appreciated by one of ordinary skill in the art, when the image is a perfect circle, $A=\pi(P/2\pi)^2=P^2/4\pi$ and $s=1$. When the area of the image is 0 (i.e., the image is a line or a curve) $s=0$.

Unless otherwise defined, "sphericity," as used herein, refers to two-dimensional sphericity.

It is recognized that the "two dimensional" sphericity is, to a good approximation, equivalent to the "three dimensional" sphericity (ratio of volumes), provided it is calculated and averaged over many particles (say 10 or more) or many different reference planes. In such event, starting from the "two dimensional" sphericity, s, the "three dimensional" sphericity can be defined as the cubic root of $s^2$.

According to a preferred embodiment of the present invention the sphericity of the particle is at least 80% more preferably at least 85%.

The zeta potential of the nanoparticles of the present invention may range from −10 to −75 mV and more preferably from −25 to −50 mV. Thus, the nanoparticles of the present invention may be negatively charged.

The particles generated according to the method of the present invention are substantially homogeneous, i.e. are all of a uniform shape and size. According to one embodiment the nanoparticle population does not comprise nanoparticles which differ by more than 5%, 10%, 20% or 30% from the size of the average nanoparticle in the population.

An exemplary homogeneous population of particles contemplated by the present invention is as follows:

particles comprising a core of siRNA and cationic molecules and a shell comprising targeting moieties (e.g. HA), wherein each of the particles of the population of particles comprises a zeta potential of about −40 mV and wherein each of the particles of the population of particles is about 100-300 nm in diameter when in solution.

Another exemplary homogeneous population of particles contemplated by the present invention is as follows:

particles comprising a core of miRNA and cationic molecules, and a shell comprising targeting moieties (e.g. HA), wherein each of the particles of the population of particles is about 30-50 nm in diameter when in solution.

As mentioned, the particles of the present invention can be engineered such that they target cancer cells and/or cancer stem cells.

Thus, according to another aspect of the present invention there is provided a method of treating cancer in a subject in need thereof, the method comprising administering to the subject a therapeutically effective amount of particles, the particles being generated according to the methods described herein, thereby treating the cancer.

As used herein, the term "cancer" refers to a disease or disorder resulting from the proliferation of oncogenically transformed cells.

Exemplary cancers which may be treated according to the present invention include, but are not limited to tumors of the gastrointestinal tract (colon cancer, rectum cancer, anal region cancer, colorectal cancer, small and/or large bowel cancer, esophageal cancer, stomach cancer, pancreatic cancer, gastric cancer, small intestine cancer, adenocarcinoma arising in the small intestine, carcinoid tumors arising in the small intestine, lymphoma arising in the small intestine, mesenchymal tumors arising in the small intestine, gastrointestinal stromal tumors), gallbladder carcinoma, Biliary tract tumors, prostate cancer, kidney (renal) cancer (e.g., Wilms' tumor), liver cancer (e.g., hepatoblastoma, hepatocellular carcinoma), hepatobiliary cancer, biliary tree cancer, tumors of the Gallbladder, bladder cancer, embryonal rhabdomyosarcoma, germ cell tumor, trophoblastic tumor, testicular germ cells tumor, immature teratoma of ovary, uterine, epithelial ovarian, sacrococcygeal tumor, choriocarcinoma, placental site trophoblastic tumor, epithelial adult tumor, ovarian cancer, cervical cancer, cancer of the vagina, cancer of the Vulva, lung cancer (e.g., small-cell and non-small cell lung carcinoma), nasopharyngeal, breast cancer, squamous cell carcinoma (e.g., in head and neck), neurogenic tumor, astrocytoma, ganglioblastoma, neuroblastoma, lymphomas (e.g., Hodgkin's disease, non-Hodgkin's lymphoma, B cell, Burkitt, cutaneous T cell, histiocytic, lymphoblastic, T cell, thymic, cutaneous T-cell lymphoma, primary central nervous system lymphoma), gliomas, medullary thyroid carcinoma, testicular cancer, brain and head/neck cancer, gynecologic cancer, endometrial cancer, germ cell tumors, mesenchymal tumors, neurogenic tumors, cancer of the bladder, cancer of the ureter, cancer of the renal pelvis, cancer of the urethra, cancer of the penis, cancer of the testis, cancers of the uterine body, endometrial carcinoma, uterine sarcoma, peritoneal carcinoma and Fallopian Tube carcinoma, germ cell tumors of the ovary, sex cord-stromal tumors, cancer of the endocrine system, thyroid tumors, medullary thyroid carcinoma, thyroid lymphoma, parathyroid tumors, adrenal tumors, pancreatic endocrine tumors, sarcomas of the soft tissue and bone, benign and malignant mesothelioma, malignant peritoneal mesothelioma, malignant mesothelioma of the Tunica Vaginalis Testis, malignant mesothelioma of the Pericardium, skin cancer, cutaneous melanoma, intraocular melanoma, neoplasms of the central nervous system, medulloblastomas, meningiomas, peripheral nerve tumors, Pineal region tumors, pituitary adenomas, craniopharyngiomas, acoustic neuromas, Glomus Jugulare tumors, Chordomas and Chondrosarcomas, Hemangioblastomas, Choroid Plexus Papillomas and Carcinomas, spinal axis tumors, leukemia, and chronic leukemia.

The term "subject" refers to animals, typically mammals, including human beings.

The particles of the present invention can be administered to a subject per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the particles comprising the polynucleotide agent accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, inrtaperitoneal, intranasal, or intraocular injections.

Alternately, one may administer the pharmaceutical composition in a local rather than systemic manner, for example, via injection of the pharmaceutical composition directly into a tissue region of a patient.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (particle composition) effective to prevent, alleviate or ameliorate symptoms of a disorder (e.g., cancer) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p.1).

Dosage amount and interval may be adjusted individually to provide plasma or brain levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein the term "about" refers to ±5%.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween. It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique"by Freshney, Wiley-Liss, N.Y. (1994), Third Edition; "Current Protocols in Immunology" Volumes Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

DOTAP-Based Particles

Material and Methods

Lipids (DOTAP, and Cholesterol) was purchased from Avanti Polar Lipids Inc. (Alabaster, Ala., USA); HSPC was purchased from LIPOID, Germany Oligofectamine™ (from Invitrogen); human recombinant protamine (from Abnova); Linear polyethylene imine (PEI) was purchased from Sigma. Hyaluronan, Mw 751 KDa, intrinsic viscosity: 16 dL/g (Genzyme cooperation, Cambridge, Mass.); FITC-HA was obtained from Calbiochem (Germany). Cy3-siRNAs were obtained from Qiagen; non-labeled (target specific against cyclin D1, RAS, HMGA2 or MYC or scarmled) siRNAs were obtained from Dharmacon. 1-Ethyl-3-(3-dimethylaminopropyl) carbodimide (EDC); Boric acid and Borax (sodium tetraborate*10H$_2$O) were purchased from Sigma-Aldrich Co. (St. Louis, Mo., USA). $^3$H-HA was purchased from American Radiolabeled Chemicals Inc. (St. Louis, Mo., USA). Cell culture plates and were from Corning Inc. (Corning, N.Y.). Materials for cell cultures were obtained from Biological Industries Co. (Beit Haemek). Dialysis tubing (molecular weight cutoff of 12,000-14,000) was purchased from Spectrum Medical Industries (Los Angeles, Calif.). Polycarbonate membranes were purchased from Nucleopore (Pleasanton, Calif.). All other reagents were of analytical grade.

Preparation of siRNAs and miRNA mimetic (antagomirs):

Cy3-siRNA scrambled sequence was from Qiagen. Cyclin D1 siRNA and negative control siRNAs (scrambled sequences) were purchased from Dharmacon and were previously reported [Peer et al., Science 319, 627-630 (2008)]. RAS, HMGA2 or MYC siRNAs were previously published [Yu et al., Cell 131, 1109-1123 (2007)] and were purchased from Dharmacon.

Preparation of H-mers (Hyaluronic Acid-Coated Nanoparticle) Encapsulating siRNAs—Method 1

Preparation of DOTAP-based particles: Hydrogenated phosphatidylcholine (HSPC), cholesterol and dioleoyl trimethylammonium propane (DOTAP) at mole ratio of 45:33:22 at 5 mg/mL lipid concentration, were prepared by the traditional lipid-film method [Peer, D., et al Biochim Biophys Acta 1612, 76-82 (2003); Peer, D. & Margalit, R. Archives of biochemistry and biophysics 383, 185-190 (2000)]. Briefly, the lipids were dissolved in ethanol at 60° C. for 20 minutes and then evaporated to dryness under reduced pressure in a rotary evaporator (Buchi, Swizerland). Then the thin lipid film was hydrated by the swelling solution that consisted of buffer alone (PBS), at a pH of 7.4. This was followed by extensive agitation using a vortex device and a 2-hour incubation in a shaker bath at 37° C. Small Unilamellar Vesicles (SUV) were obtained by extrusion of the MLV, operating the Lipex extrusion device at 60° C. and under nitrogen pressures of 200 to 500 psi. The extrusion was carried out in stages using progressively smaller pore-size membranes, with several cycles per pore-size to a final size of 30 nm in diameter. Size distribution at 1:1000 dilution of the stock (i.e. 5 μg/mL) was 25±4 nm in diameter with a zeta potential of +72.3±6.1 mV.

Preparation of oligofectamine™, PEI™ and protamine complexes: The preparation of oligofectamine or PEI complexes was done as recommended by their manufactures. Briefly, 60 pmole of siRNAs were diluted in 50 μl of Opti-MEM™ reduced serum medium without serum and mixed gently. Branched PEI or oligofectamine were diluted (3 μl in 12 μl of Opti-MEM I Medium). This was mixed gently and incubated for 5 minutes at room temperature. The diluted siRNA was combined with the diluted Oligofectamine™ (total volume is 68 μl), mixed gently and incubated for 20 minutes at room temperature to allow the siRNA:oligofectamine complexes to form. For protamine (human recombinant), the same protocol was used, but the ratio of the protamine to siRAN was 5:1 mole ratio. (The protamine tube was added to the siRNA tube to generate the complex).

Preparation of acetate activated hyaluronic acid (HA): 8 mg of activated HA was weighed in a glass vial and dissolved in 8 ml acetate buffer 0.1 M pH 4.0 (1 mg/ml). The mixture was stirred for a few minutes at 37° C. until the HA was completely dissolved. EDC was added in excess 40 mg (5mg EDC/mg HA). The solution was stirred at 37° C. for 2 hours.

Preparation of lipid-siRNA suspensions: 3 μl of the particles (5 μg/mL) were added to 12 μl of DMEM. The suspension was mixed gently and incubated for 5 minutes at room temperature (RT). 3 μl of siRNAs (100 μM, 300 pmole) were added to 50 μl of DMEM. The solution was mixed gently and incubated for 5 minutes at RT. The particle solution was added to the siRNAs solution and incubated for 20 minutes at RT under gentle stirring.

Assembly of Hyaluromers (per well of 24 well plate):13.6 μl activated HA (in ratio of 1:5 v/v (HA:complex)) was added to 68 μl of the lipid-siRNA complex and incubated at 37° C. for 2 hours under gentle stirring. 18.3 μl of DMEM was added to a final volume of 100 μl (per well). The pH was corrected to pH 7.0.-7.4.

This system was scaled up 1000-fold using 5 mg/ml particles and up to 0.3 μmole.

Preparation of H-mers (Hyaluronic Acid-Coated Nanoparticle) Encapsulating siRNAs—Method 2

Preparation of DOTAP-based particles: as described herein above.

Preparation of DDW activated HA: 8 mg of HA was weighed in a glass vial and dissolved in 8 ml DDW (1 mg/ml). This was stirred for a few minutes at 37° C. until the HA was completely dissolved. EDC was added in excess 40 mg (5 mg EDC/mg HA). The solution was stirred at 37° C. for 2 hours.

Preparation of lipid-siRNA suspensions: as described herein above.

Assembly of Hyaluromers (per well of 24 well plate): as described herein above.

This system could not be scaled up more than 10-fold, i.e. particles conc. 50 μg/mL and siRNAs at 3 nmole only.

Particle surface topography: The measuring of particle surface topography was performed by NanoScope IIIa MultiMode AFM of Digital Instruments (USA) operating in taping mode. A short time before the AFM measurements, the H-mers samples were diluted 1:10 and a small drop (~50 μl) was placed on silicon oxide. After several minutes the sample was dried under fine beam of nitrogen and taken for screening. The measurements of H-mers were performed at room temperature and atmospheric pressure using non-contact method and triangular silicon tips (R<20 nm) at a scan rate of 1 Hz. The gap between tip and sample was 10-100Å. 512 lines were scanned in two segments over the sample area to form two-dimensional range.

E-SEM (environmental Scanning electron microscopy) was performed as well.

Particle hydrodynamic diameter and zeta potential measurements: The diameter of the H-mers were measured on a Malvern Zetasizer nano ZS Zeta potential and Dynamic Light Scattering Instrument (Malvern Instruments Ltd., Southborough, Mass.) using the automatic algorithm mode and analyzed with the PCS 1.32a. All measurements were performed in 0.01M NaCl, pH 6.7, at room temperature.

Encapsulation efficiency: Defined as the ratio of entrapped siRNA to the total siRNA in the system, encapsulation efficiency can be determined by centrifugation. Samples of complete H-mers preparation (i.e., containing both encapsulated and unencapsulated siRNAs) were centrifuged in a mini-ultra centrifugation (Sorval, Discovery 150M). The supernatant, containing the unencapsulated siRNA, was removed and the pellet, containing the particles with encapsulated siRNAs, was resuspended in siRNA-free buffer. siRNA was assayed by the ribogreen assay (Invitrogen) in the supernatant and in the pellet, as well as in the complete preparation, from which the encapsulation efficiency and conservation of matter can be calculated as previously described [Peer et al., Science 319, 627-630 (2008)].

Cell lines for in vitro study: Breast T-IC (BT-IC) can be repeatedly passaged as nonadherent spheres in serum-free medium ("mammospheres"), lack expression of differentiation markers (cytokeratins, smooth muscle actin and mucin-1) and are CD44+CD24-. However, these markers are not capable of distinguishing BT-IC from early progenitor cells (EPC). The reasons for the relative resistance of BT-IC to chemotherapy are likely multifactorial, but are still largely undefined. One mechanism is enhanced drug efflux (measured as a drug-effluxing side population SP by flow cytometry). BT-IC and EPC have enhanced expression of the ABCG2 multidrug transporter and melanoma stem cells over-express another multidrug transporter, ABCB5.

A human breast cancer cell line (SK-3rd) was generated which was highly enriched for BT-IC by in vivo passage of SKBR3 cells under selective pressure of epirubicin. These cells stably maintain stem cell properties (self-renewal, multipotency) and can be expanded indefinitely in vitro under sphere-forming conditions to provide unlimited numbers of cells for further study. SK-3rd cells form tumors in NOD/SCID mice using 100-fold fewer cells than SKBR3, and unlike SKBR3, the tumors are metastatic. Moreover, these cells are relatively resistant to chemotherapy.

HL60 human acute myeloid leukemia (AML) cells were also used as a model for leukemic stem cells.

Flow cytometry studies: When fluorescently labeled siRNAs were used, the amount of $Cy3^+$ cells were quantified using a BD FACScan system.

Image acquisition and processing: Confocal imaging was performed using a Biorad Radiance 2000 Laser-scanning confocal system (Hercules, Calif.) incorporating with an Olympus BX50BWI microscope fitted with an Olympus 100× LUMPlanFL 1.0 water-dipping objective. Image acquisition was performed using Laserscan 2000 software and image processing was performed with Openlab 3.1.5 software (Improvision, Lexington, Mass.).

Interferon assay: HL60 cells ($1\times10^6$ cells/ml) were mock treated or treated for 48 hours with H-mers entrapping 1,000 pmol control (negative)-siRNA or 5 µg/ml poly (I:C). Expression of IFN or interferon responsive genes was examined by quantitative RT-PCR.

In vitro transfection of siRNAs: Cells (SKBR3, or SK-$3^{rd}$, or HL-60) that had been pre-cultured overnight at 37° C., 5% $CO_2$ in 24-well microtiter plates ($2.5\times10^5$ cells in 200 µl media/well) were given aliquots (50 µl/well) of H-mers entrapping siRNAs or 25- appropriate controls. Cells were cultured for 6 to 72 hours at 37° C., 5% $CO_2$ and subjected to flow cytometry and/or real time RT-PCR analyses.

Quantitative RT-PCR: Quantitative RT-PCR using a ABI one step plus device was carried out as previously described. Primers for human OAS1, and IFN-β, were used as previously described [Peer et al., Science 2008, 319(5863):627-30]. Primer sequences were as follows:

```
Human Cyclin D1 (CCND1)
Forward:
                                (SEQ ID NO: 1)
TGCTCCTGGTGAACAAGCTCAAGT Reverse:
                                (SEQ ID NO: 2)
TGATCTGTTTGTTCTCCTCCGCCT GAPDH
Forward:
                                (SEQ ID NO: 3)
GACCCCTTCATTGACCTCAAC Reverse:
                                (SEQ ID NO: 4)
CTTCTCCATGGTGGTGAAGA STAT1
Forward:
                                (SEQ ID NO: 5)
GTGCATCATGGGCTTCATCAGCAA Reverse:
                                (SEQ ID NO: 6)
TAGGGTTCAACCGCATGGAAGTCA
```

Results

Preparation and Structural Characterization of Hyaluronic Acid-Coated Nanoparticle (H-mer) Entrapping siRNAs H-mer entrapping siRNAs were prepared as detailed in the experimental section. Several positively charged materials were used for the self-assembly process with siRNAs among them DOTAP, PEI, oligofectamine™ and human recombinant protamine.

DOTAP H-mers generated with acetate buffer formed a uniform globular nanoparticle shape as demonstrated by their topography (FIG. 1A) and their hydrodynamic diameter (Table 1). Measuring their zeta potential (Table 1) indicates their stability in a physiological pH (by not forming aggregates at these conditions). In addition, H-mers entrapped high amounts of RNAi payloads (Table 1).

TABLE 1

| H-mer type (positively charge residue) | Hydrodynamic diameter (nm) | Zeta potential (mV) | Number of siRNAs molecules in a particle |
|---|---|---|---|
| DOTAP-DDW | 179 ± 100 | −20.32 ± 3.2 | 5000 |
| DOTAP-AB | 103 ± 9 | −39.1 ± 4.0 | 11,400 |
| Oligofectamine ™-DDW | 145 ± 89 | −17.4 ± 3.9 | 4800 |
| Oligofectamine ™-AB | 117 ± 10 | −34.4 ± 4.7 | 7900 |
| PEI-DDW | 253 ± 112 | −16.1 ± 2.0 | 3000 |
| PEI-AB | 189 ± 41 | −32.1 ± 4.6 | 5500 |
| Protamine-DDW | 220 ± 98 | −18.4 ± 3.8 | 4000 |
| Protamine-AB | 167 ± 16 | −28.9 ± 2.7 | 7300 |

All measurements were performed at room temp. Lyophilized H-mers entrapping siRNAs were resuspended in 0.01 M NaCl, pH 6.7. siRNAs was quantified by ribogreen assay (Invitrogen) as previously reported[21]. Data represent an average of 3 batches±SD.

It is clear from these measurements that the preparation of the H-mer in acetate buffer stabilize their structure. The particle size distribution of the H-mer made in acetate buffer is much smaller then the H-mer made in DDW.

It may be concluded that the low pH that drives the assembly process into a particle is essential for increasing binding of amines form the positively charged materials to the carboxylic groups on the activated HA.

Transfection in CD44 Expressing Cells for Screening the Best Formulation

Human pancreatic adenocarcinoma (PANC-1) cells expressing $CD44^{high}$ were used to determine the transfection efficiency of the different formulations (all were made with DOTAP as the cationic entity in the formulation). Representative images are shown in FIGS. 2A-F and in Table 2.

The data are an average±SD of three independent experiments.

TABLE 2

| Cell line name All express $CD44^{high}$ | Transfection efficiency H-mer (AB) | Transfection efficiency H-mer (DDW) |
|---|---|---|
| PANC-1 (human pancreatic adenocarcinoma) | 85% ± 10 | 20% ± 8 |
| NCI-ADR (human ovarian cacinoma resistant to DOX) | 90% ± 15 | 25% ± 10 |
| OVCAR8 (human ovarian carcinoma) | 87% ± 10 | 20% ± 10 |

Selective Delivery of siRNAs to Tumor Initiating Cells (T-IC, Cancer Stem Cells) Using Particles Generated from DOTAP as the Cationic Entity Generated in Acetate Buffer (H-Mers)

In order to examine the delivery of siRNA selectively in cancer stem cells (therefore addressing specificity) three types of cells were used: SK-3$^{rd}$ breast cancer stem cells derived from SKBR3, which express high amounts of CD44 (CD44$^{high}$); SKBR3 cells which express CD44 (CD44$^+$) and CV-1 cells that do not express CD44 (CD44$^-$). In order to simulate in vivo conditions, cells where exposed to H-mers or control (oligifectamine, Invitrogen, a commercially available cationic liposome used as a transfection reagent non-selective to cells) for a short period of time (3 hours). Then cells were washed twice and incubated for additionally 6 hours prior to a flow cytomery analysis.

Oligofectamine™ was mixed with 50 nM Cy3-siRNAs according to the manufacture guidelines or H-mers entrapping same siRNAs amounts (50nM).

The results are summarized in Table 3 herein below.

TABLE 3

| | % of Cy3 positive cells (quantified by flow cytometry) | | |
|---|---|---|---|
| | SK-3$^{rd}$ (CD44$^{high}$) | SKBR3 (CD44$^+$) | CV-1 (CD44$^-$) |
| Oligofectamine ™ | 67.5 ± 5.0 | 89.2 ± 5.3 | 90.4 ± 7.5 |
| H-mers | 91.3 ± 9.5 | 83.5 ± 7.3 | 2.7 ± 0.9 |

As clearly demonstrated in Table 3, H-mers delivered more siRNAs to the breast cancer initiating (SK-3$^{rd}$) cells than oligofectamine™. In SKBR3 cells (also expressing high amounts of CD44, but half a log less than SK-3$^{rd}$ cells), high siRNAs uptake was demonstrated. However, in CV-1 cells, that do not express CD44 (based on flow cytometry, using a labeled mAb against CD44, clone:1M7) siRNAs uptake using H-mer was at the background level.

A similar result was obtained when H-L60 cells (human leukemic cancer stem cells) were used (data not shown).

H-mers can selectively knockdown a reference gene in T-IC.

To test whether the H-mers can selectively induce silencing of a reference gene, the present inventors incorporated Cyclin D1 (CyD1) siRNAs or control-siRNAs into H-mers and transduced HL60 cells as described in the Materials and Methods section. The results are summarized in FIG. 3. FIG. 3 show selective knockdown of CyD1 in leukemic stem cells of more than 80%, while control siRNAs delivered via H-mers had no effect on CyD1 mRNA level. In addition, when CV-1 cells were used, no significant changes in CyD1 mRNA levels were observed supporting the fact that H-mers operate in a CD44-dependent manner.

H-mers entrapping a mixture of siRNAs against several oncogenes selectively eradicate T-IC.

In order to test the potency of eradicating T-IC using siRNAs entrapped in H-mers, the protocol was adapted to simulate the in vivo environment, i.e. short exposure of the cells to the different formulations (4 hours) followed by extensive washing and additional incubation of drug-free media for additional 72 hours. Cell survival was monitored using XTT assay.

FIG. 4 represent the survival of different cells (SK-3$^{rd}$ CD44$^{high}$, SKBR3 CD44$^+$, and CV-1(CD44$^-$) using a combination of siRNAs (RAS, HMGA2 or MYC) entrapped in H-mers or controls (oligofectamine™ as a non-selective transfection reagent and control siRNA delivered via H-mers).

The results of the oligofectamine™ transfected cells suggest that all the tested cell types are amendable to transfection. H-mers selectively deliver the siRNAs mixture that accumulate in cell death in CD44 expressing cells (including SK-3$^{rd}$, cancer stem cells), but not in cells lacking CD44 expression as in the case of CV-1 cells.

In addition, the use of H-mers themselves do not cause any toxicity observed via this survival assay (FIG. 4, grey columns).

H-mers entrapping siRNAs do not induce unwanted immune response.

In order to test whether the H-mers caused an interferon response; HL60 cells originating from human leukemic stem cells were analyzed for interferon responses. The results are provided in FIG. 5.

H-mers entrapping 1 nmole of control siRNA did not induce interferon response when cultured up to 48 hours in the presence of HL60 cells (FIG. 5). In contrast, the use of oligofectamine™ as an siRNA condenser did induce an unwanted immune response, as well as non-encapsulated. siRNA. Poly I:C was used as a positive control.

H-Mers Entrapping miRNAs

DOTAP-containing particles were also formulated to comprise single stranded miRNA mimetic (antagomirs). The resulting H-mer entrapping antagomirs shows smaller particles in the range of 35nm in diameter (vs.~100 nm when siRNAs are used) as summarized in Table 4 herein below and illustrated in FIG. 6.

TABLE 4

| Batch # | Hydrodynamic diameter (nm) Mean ± SD | # of miRNA molecules entrapped |
|---|---|---|
| 1 | 39 ± 6 | 6000 |
| 2 | 42 ± 8 | 6200 |
| 3 | 37 ± 4 | 6000 |

Each value represent the mean ± SD of three independent measurements in the Malvern Nano ZS zetasizer.
The antagomirs were purchased from Dharmacon. The number of antagomirs molecules were assayed using a Ribogreen (Invitrogen).

Example 2

DLPE:DLPG Based Particles

Material and Methods

Materials: Lipids (1,2-Dilauroyl-sn-Glicero-3-Phosphoethanolamine (DLPE) and 1,2-Dilauroyl-sn-Glicero-3-Glycerol (DLPG)) were purchased from Avanti Polar Lipids Inc. (Alabaster, Ala., USA). Hyaluronan, Mw 751KDa, intrinsic viscosity: 16 dL/g (Genzyme cooperation, Cambridge, Mass.); FITC-HA was obtained from Calbiochem® (Germany). Cy3-siRNAs were purchased from Qiagen; non-labeled siRNAs were from Dharmacon. Paclitaxel, semisyntetic from *Taxus* sp., minimum 97%; 1-Ethyl-3-(3-dimethylaminopropyl) carbodimide (EDC); Boric acid and Borax (sodium tetraborate*10H$_2$O) were purchased from Sigma-Aldrich Co. (St. Louis, Mo., USA). $^3$H-Paclitaxel Phosphatidylethanolamine(arach-1-$^{14}$C) and $^3$H-HA were purchased from American Radiolabeled Chemicals Inc. (St. Louis, Mo., USA). Cell culture plates were obtained from Corning Inc. (Corning, N.Y.). Materials for cell cultures were obtained from Biological Industries Co. (Beit Haemek, Israel). Dialysis tubing (molecular weight cutoff of 12,000-14,000) was purchased from Spectrum Medical Industries (Los Angeles, Calif.). Polycarbonate membranes were purchased from Nucleopore (Pleasanton, Calif.). All other reagents were of analytical grade.

Preparation of hyalumers encapsulating siRNAs: Particles were prepared in ratios of 10:1 (mole/mole) DLPE:DLPG, 1:10 (w/w) HA:lipids and 1:100-1:10 siRNA:lipids (mole/mole). Other contemplated ranges include 1:850 (mole/mole) siRNAs:lipids.

Activated HA: 1.33mg HA was dissolved in 4 ml acetate buffer pH=4.5 100 mM (0.33 mg/ml). EDC was added in excess 26.67 mg (20 mg EDC/mg HA) and the mixture was shaken at 37° C. for 2 hours.

Preparation of lipid-siRNA suspensions: 4.5 mg of DLPE and 0.5 mg DLPG were weighed and put it into 50 ml plastic tube. 3.5 ml of Borate Buffer 0.1M pH=9.0 was added to the dry lipid. The suspension was heated at above Tm (about 70° C.) for at least 2 hours following which it was sonicated for 1 min×5 times in a probe sonicator. The suspension was then extruded 10 times via 0.1 µm polycarbonate filter in Lipex extruder with jacket heated to 70° C. 100 µl of siRNA solution (100 µM) was added together with 1.5 m1 activated HA. Following an overnight incubation at 37° C. with shaking dialysis was performed using MWCO 12-14,000 membranes.

Particle surface topography: as described for Example 1.

Particle hydrodynamic diameter and zeta potential measurements: as described in Example 1.

Encapsulation efficiency: as described in Example 1.

Preparation of siRNAs: as described herein above.

In vitro study: as described herein above.

Flow cytometry studies: as described herein above.

Image acquisition and processing: as described herein above.

In vitro transfection of siRNAs: as described herein above.

Results

Preparation and structural characterization of hyalumers entrapping siRNAs:

Hyaluomers entrapping siRNAs were prepared as detailed in the experimental section. They formed a uniform globular nanoparticle shape as demonstrated by their topography (FIG. 7) and their hydrodynamic diameter (Table 1). Measuring their zeta potential (Table 5) indicates their stability in a physiological pH (by not forming aggregates at these conditions). In addition, hyalumers entrapped high amounts of RNAi payloads (Table 5). The high batch to batch consistency is reflected by the reproducibility in three independent preparations (Table 5).

TABLE 5

| Hyalumers batch # | Hydrodynamic diameter (nm) | Zeta potential (mV) | Efficency of siRNA entrapment (%) |
| --- | --- | --- | --- |
| 1 | 103 ± 7 | −37.5 ± 3.4 | 94.1 ± 5.1 |
| 2 | 115 ± 9 | −38.1 ± 4.0 | 93.5 ± 4.3 |
| 3 | 93 ± 8 | −35.4 ± 3.8 | 96.0 ± 4.8 |

All measurements were performed at room temperature. Lyophilized hyalumers entrapping siRNAs were resuspended in 0.01M NaCl, pH 6.7. siRNAs was quantified by ribogreen assay (Invitrogen).

Hyalumers (generated to incorporate FITC-HA) were shown to deliver siRNAs to HL60 cells (leukemic stem cells) as seen in FIGS. 8A-C.

As clearly seen from FIGS. 8A-C, only hyalumers can deliver siRNAs into leukemic stem cells, but not a commercially available reagent oligofectamine™ that was also used, or siRNAs alone.

Example 3

Particles of embodiments of the present invention can target AML primary cells and Human ovarian adenocarcinoma cells.

Materials and Methods

Particles for targeting AML primary cells: Particles were generated as described in Example 1 and loaded with cyclin D1, Cy3 labeled siRNA.

Particles for targeting Human ovarian adenocarcinoma cells: 60% DOTAP 30% cholesterol, 10% DLPE at 10 mg/mL were dissolved in ethanol and heated until a clear solution was obtained. Afterwards the lipids were dried in a buchi evaporator and rehydrated in borate buffer. The solution was then voretexed vigorously and placed in a shaker for 2 hours at 37° C.

Lipid particle formation was achieved by passing the lipids in an extruder with different filters (400 nm twice, 200 nm twice, 100 nm twice, 50 nm 10 times) final particles' size was ~80 nm. The ULV were kept in 4° C. until the day of the experiment For assembly, 112 µl of Opti-MEM was added to small glass vial together with 7 µl of siRNA to human P glycoprotein (Pgp) (20 µM stock). After five minutes incubation, 18.5 µl of diluted lipids (1 mg/ml) were added. Following another 20 minutes at room temperature, 18.5 µl of diluted HA (0.2 mg/ml) was added, which had previously been preactivated under acidic conditions as described in Example 1. The mixture was incubated for 16 hours at room temperature.

Transfection of AML primary cells: Freshly isolated blood from AML patients was separated on a Ficoll gradient density (PBMC). Cells were further sorted using a FACSAria cell sorter (CD3-CD19−/CD34+CD38−) on ice. Then cells ($2.5 \times 10^5$ cells) were seeded into 6 well plate in 2.5 mL RPMI 1640 full media (containing 10% serum). Particles were prepared as detailed in Example 1 with 150 pmol siRNAs (total con.50 nM) was resuspended in 500µl of serum-free RPMI media and placed on the cells. Total volume was 3 mL. RT-PCR was used to determine the amount of mRNA from untreated and treated AML cells.

Transfection of Human ovarian adenocarcinoma cells: Human ovarian adenocarcinoma cells were grown in 24 well plate at a concentration of $0.1 \times 10^6$ cell/well in complete medium without antibiotics. After 24 hours the medium was removed and replaced with serum free RPMI medium. The cells were then treated with 110 µls of the hyalumer solution. 5 hours post incubation with antibiotic-free, serum-free RPMI, full media with serum was added (final serum concentration 10%). Following overnight incubation, the medium was replaced with complete RPMI medium. After 72 hours Pgp protein levels were analyzed by flow cytometry.

Results

Hyalumer delivery to AML primary cells: As indicated in FIGS. 9A-C and FIG. 10, particles according to embodiments of the present invention are capable of delivering siRNA to AML primary cells and inducing potent gene silencing.

Figure 11:
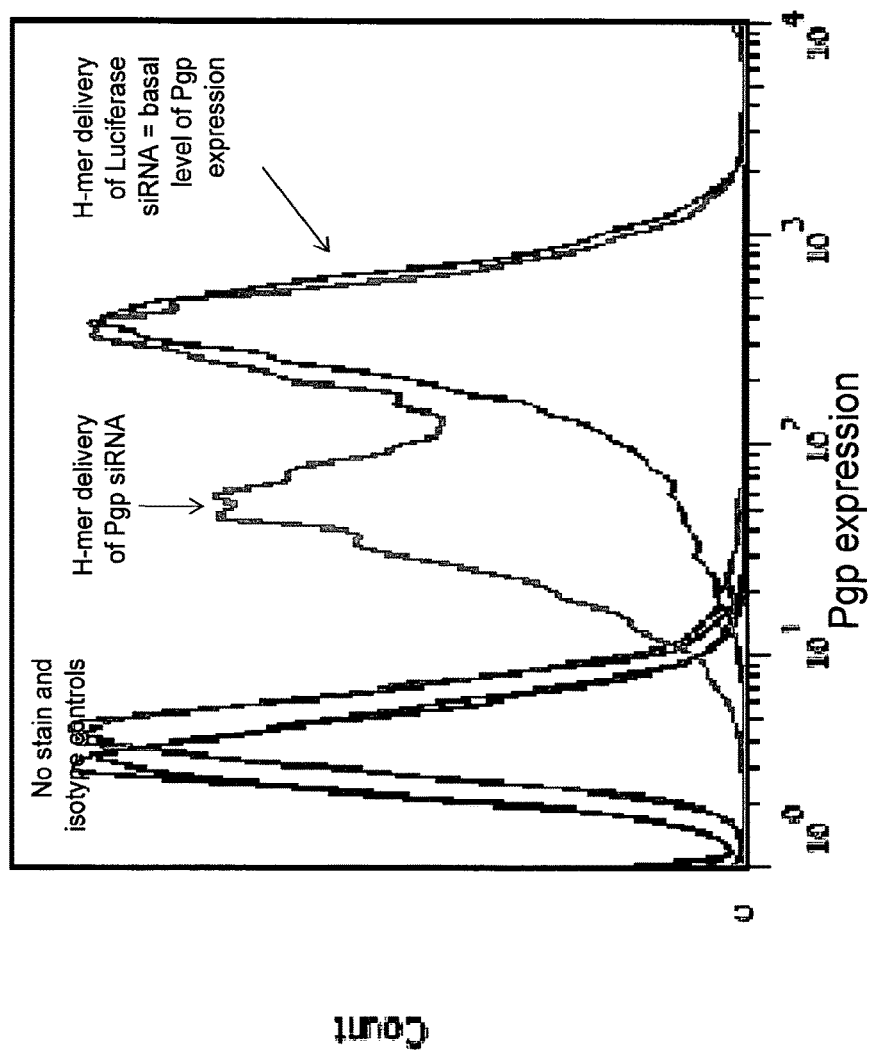
FIG. 11 is a graph illustrating results of the flow cytometry analysis indicating the reduction of P-glycoprotein (Pgp) expression in human ovarian adenocarcimona cell line (NCI-ADR/RES).

Hyalumer delivery to human ovarian adenocarcinoma cells: As indicated in FIG. 11, particles according to embodiments of the present invention are capable of delivering siRNA to human ovarian adenocarcinoma primary cells and inducing potent gene silencing.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A particle comprising a core and a shell, wherein the core comprises 1,2-Dilauroyl-sn-Glicero-3-Phosphorylglycerol (DLPG), a lipid having an amino group which is 1,2-Dilauroyl-sn-Glicero-3-Phosphoethanolamine (DLPE), a polynucleotide, and optionally a cationic lipid and/or cholesterol; wherein the shell comprises a glycosaminoglycan targeting moiety; and wherein the particle is not a liposome.

2. The particle of claim 1, wherein the glycosaminoglycan targeting moiety is selected from the group consisting of hyaluronic acid (HA), keratan sulfate, chondroitin sulfate, heparin sulfate, heparan sulfate, dermatin sulfate, salts, and mixtures thereof.

3. The particle of claim 1, wherein the polynucleotide comprises RNA or DNA.

4. The particle of claim 1, wherein the polynucleotide is selected from a single stranded and a double stranded polynucleotide.

5. The particle of claim 1, wherein the polynucleotide comprises an RNA silencing agent.

6. The particle of claim 5, wherein the RNA silencing agent is selected from the group consisting of an siRNA, miRNA, an antisense oligonucleotide, and a ribozyme.

7. The particle of claim 1, wherein the cationic lipid is selected from the group consisting of dioleoyl trimethylammonium-propane (DOTAP); N-[1-(2,3-dioleyloxy)propyl]-N , N, N-trimethlylammonium chloride (DOTMA); dimethyldioctadecylammonium (DDAB); 1,2-dilauroyl-sn-glycero-3-ethylphosphocholine; 1,2-di-(9Zoctadecenoyl)-3-dimethylammonium-propane; and 38-[N-(N',N'-dimethylaminoethane)carbamoyl]cholesterol hydrochloride (DC-Cholesterol).

8. The particle of claim 1, wherein the core comprises DOTAP, and cholesterol.

9. The particle of claim 1, further comprising at least one additional targeting moiety, said additional targeting moiety being selected from the group consisting of an antibody, an antibody fragment, a receptor ligand and an aptamer.

10. The particle of claim 1, wherein the particle is a nanoparticle of about 1 nm to about 500 nm in size.

11. A method for downregulating a gene of interest in a target cell, comprising administering the particle of claim 1 to the target cell.

12. The method of claim 11, wherein the target cell expresses CD44.

13. The method of claim 11, wherein the gene of interest is an oncogene and/or a gene associated with cell viability.

14. A method for treating cancer in a subject in need thereof, the method comprising administering to the subject a particle according to claim 1.

* * * * *

SEQUENCE LISTING

<160> NUMBER OF SEQ ID NOS: 6

<210> SEQ ID NO 1
<211> LENGTH: 24
<212> TYPE: DNA
<213> ORGANISM: Artificial Sequence
<220> FEATURE:
<223> OTHER INFORMATION: Single strand DNA oligonucleotide

<400> SEQUENCE: 1
tgctcctggt gaacaagctc aagt                                              24

<210> SEQ ID NO 2
<211> LENGTH: 24
<212> TYPE: DNA
<213> ORGANISM: Artificial Sequence
<220> FEATURE:
<223> OTHER INFORMATION: Single strand DNA oligonucleotide

<400> SEQUENCE: 2
tgatctgttt gttctcctcc gcct                                              24

<210> SEQ ID NO 3
<211> LENGTH: 21
<212> TYPE: DNA
<213> ORGANISM: Artificial Sequence
<220> FEATURE:
<223> OTHER INFORMATION: Single strand DNA oligonucleotide

<400> SEQUENCE: 3
gaccccttca ttgacctcaa c                                                 21

<210> SEQ ID NO 4
<211> LENGTH: 20
<212> TYPE: DNA
<213> ORGANISM: Artificial Sequence
<220> FEATURE:
<223> OTHER INFORMATION: Single strand DNA oligonucleotide

<400> SEQUENCE: 4
cttctccatg gtggtgaaga                                                   20

<210> SEQ ID NO 5
<211> LENGTH: 24
<212> TYPE: DNA
<213> ORGANISM: Artificial Sequence
<220> FEATURE:
<223> OTHER INFORMATION: Single strand DNA oligonucleotide

<400> SEQUENCE: 5
gtgcatcatg ggcttcatca gcaa                                              24

<210> SEQ ID NO 6
<211> LENGTH: 24
<212> TYPE: DNA
<213> ORGANISM: Artificial Sequence
<220> FEATURE:

```
<223> OTHER INFORMATION: Single strand DNA oligonucleotide

<400> SEQUENCE: 6
tagggttcaa ccgcatggaa gtca                                          24
```